US008030515B2

(12) United States Patent
Kobayashi et al.

(10) Patent No.: US 8,030,515 B2
(45) Date of Patent: Oct. 4, 2011

(54) SULFONATE SALTS AND DERIVATIVES, PHOTOACID GENERATORS, RESIST COMPOSITIONS, AND PATTERNING PROCESS

(75) Inventors: Katsuhiro Kobayashi, Joetsu (JP); Youichi Ohsawa, Joetsu (JP); Takeshi Kinsho, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/043,683

(22) Filed: Mar. 9, 2011

(65) Prior Publication Data

US 2011/0160481 A1    Jun. 30, 2011

Related U.S. Application Data

(62) Division of application No. 11/767,783, filed on Jun. 25, 2007, now Pat. No. 7,928,262.

(30) Foreign Application Priority Data

Jun. 27, 2006   (JP) ................................. 2006-176044

(51) Int. Cl.
    C07C 309/08    (2006.01)
(52) U.S. Cl. ...................... 562/108; 562/112
(58) Field of Classification Search .................. 562/108, 562/112
    See application file for complete search history.

(56) References Cited

U.S. PATENT DOCUMENTS

| 2,806,876 | A | * | 9/1957 | Blaser et al. ................... 562/108 |
| 3,384,595 | A | * | 5/1968 | Broussalian .................. 510/495 |
| 5,705,702 | A | | 1/1998 | Osawa et al. |
| 6,048,672 | A | | 4/2000 | Cameron et al. |
| 6,261,738 | B1 | | 7/2001 | Asakura et al. |
| 6,440,634 | B1 | | 8/2002 | Ohsawa et al. |
| 6,723,483 | B1 | | 4/2004 | Oono et al. |
| 6,749,987 | B2 | | 6/2004 | Kodama et al. |
| 6,849,374 | B2 | | 2/2005 | Cameron et al. |
| 6,858,760 | B2 | | 2/2005 | Komoriya et al. |
| 6,875,556 | B2 | | 4/2005 | Harada et al. |
| 6,902,772 | B2 | | 6/2005 | Takeda et al. |
| 6,908,722 | B2 | | 6/2005 | Ebata et al. |
| 6,919,161 | B2 | | 7/2005 | Hatakeyama et al. |
| 6,949,678 | B2 | | 9/2005 | Kunimoto et al. |
| 6,994,946 | B2 | | 2/2006 | Hatakeyama et al. |
| 7,834,209 | B2 | * | 11/2010 | Junk et al. ...................... 562/111 |
| 2001/0036591 | A1 | | 11/2001 | Schulz et al. |
| 2002/0197558 | A1 | | 12/2002 | Ferreira et al. |
| 2003/0113659 | A1 | | 6/2003 | Hatakeyama et al. |
| 2004/0023176 | A1 | | 2/2004 | Harada et al. |
| 2004/0067436 | A1 | | 4/2004 | Kinsho et al. |
| 2004/0106751 | A1 | | 6/2004 | Sumida et al. |
| 2004/0157155 | A1 | | 8/2004 | Harada et al. |
| 2004/0192867 | A1 | | 9/2004 | Narita et al. |
| 2004/0241579 | A1 | | 12/2004 | Hamada et al. |
| 2005/0130060 | A1 | | 6/2005 | Kodama et al. |
| 2005/0176982 | A1 | | 8/2005 | Tomita et al. |
| 2006/0040203 | A1 | | 2/2006 | Kodama et al. |
| 2006/0074263 | A1 | | 4/2006 | Kobayashi et al. |
| 2006/0135744 | A1 | | 6/2006 | Komoriya et al. |
| 2006/0217507 | A1 | | 9/2006 | Miyazawa et al. |
| 2006/0270864 | A1 | | 11/2006 | Sumida et al. |

FOREIGN PATENT DOCUMENTS

| EP | 0043547 A1 | 1/1982 |
| JP | 4-230645 A | 8/1992 |
| JP | 07-25846 | 1/1995 |
| JP | 8311018 A | 11/1996 |
| JP | 9015848 A | 1/1997 |
| JP | 0995479 A | 4/1997 |
| JP | 9-208554 A | 8/1997 |
| JP | 9-230588 A | 9/1997 |
| JP | 9-301948 A | 11/1997 |
| JP | 2906999 B2 | 4/1999 |
| JP | 11282168 A | 10/1999 |
| JP | 2000122296 A | 4/2000 |
| JP | 2000-314956 A | 11/2000 |
| JP | 2001122850 A | 5/2001 |
| JP | 2001181221 A | 7/2001 |
| JP | 2001233842 A | 8/2001 |
| JP | 2002167340 A | 6/2002 |
| JP | 2002193887 A | 7/2002 |
| JP | 2002193925 A | 7/2002 |
| JP | 20002214774 A | 7/2002 |
| JP | 2003107706 A | 4/2003 |
| JP | 2003140332 A | 5/2003 |
| JP | 2003-252855 A | 9/2003 |
| JP | 2004-2252 A | 1/2004 |
| JP | 2004-035671 A | 2/2004 |
| JP | 2004-059844 A | 2/2004 |
| JP | 2004-083873 A | 3/2004 |
| JP | 2004-083900 A | 3/2004 |
| JP | 2004-099689 A | 4/2004 |
| JP | 2004-115762 A | 4/2004 |

(Continued)

OTHER PUBLICATIONS

Federal Register; vol. 67, No. 47; pp. 11008-11013, Monday, Mar. 11, 2002. Federal Register; vol. 67, No. 236, pp. 72854-72867, Monday, Dec. 9, 2002.
Koji Arimitsu et al., "Effect of Phenolic Hydroxyl Residues on the Improvement of Acid-Proliferation-Type Photoimaging Materials"; Journal of Photopolymer Science and Technology vol. 9, No. 1 (1996), pp. 29-30.
Koji Arimitsu et al., "Sensitivity Enhancement of Chemical-Amplification-Type Photoimaging Materials By Acetoacetic Acid Derivatives"; Journal of Photopolymer Science and Technology, vol. 8, No. 1 (1995) pp. 42-44.
Miller et al. "Deoxygenation of Sulfoxides Promoted by Electrophilic Silicon Reagents: Preparation of Aryl-Substituted Sulfonium Salts"; J. Org. Chem., vol. 53, pp. 5571-5573, (1998).
P. A. Lowe.m, "The Chemistry of Sulphonium Group Part 1"; John-Wiley & Sons (1981), pp. 267-312.
Ralph R. Demmel et al., "Journal of Photo Science and Technology", vol. 17, No. 4, pp. 587 (2004).
Robert J. DeVoe et al., "Photochemistry and Photophysics of 'Onium Salts", Advanced Photochemistry, vol. 17, John-Wiley & Son (1981).

(Continued)

Primary Examiner — Peter O Sullivan
(74) Attorney, Agent, or Firm — Westerman, Hattori, Daniels & Adrian, LLP

(57) ABSTRACT

Sulfonate salts have the formula: $HOCH_2CH_2CF_2CF_2SO_3^-$ $M^+$ wherein $M^+$ is a Li, Na, K, ammonium or tetramethylammonium ion. Onium salts, oxime sulfonates and sulfonyloxyimides derived from these salts are effective photoacid generators in chemically amplified resist compositions.

1 Claim, 2 Drawing Sheets

FOREIGN PATENT DOCUMENTS

| | | |
|---|---|---|
| JP | 2004-145048 A | 5/2004 |
| JP | 2004-190036 A | 7/2004 |
| JP | 2004-217533 A | 8/2004 |
| JP | 2004-231815 A | 8/2004 |
| JP | 2004-244439 A | 9/2004 |
| JP | 2004-252405 A | 9/2004 |
| JP | 2004-256562 A | 9/2004 |
| JP | 2004-292781 A | 10/2004 |
| JP | 2004-531749 A | 10/2004 |
| JP | 2004-307387 A | 11/2004 |
| JP | 2004-307447 A | 11/2004 |
| JP | 2004-323422 A | 11/2004 |
| JP | 2004-331853 A | 11/2004 |
| JP | 2004-331854 A | 11/2004 |
| JP | 2004-352743 A | 12/2004 |
| JP | 2004-354417 A | 12/2004 |
| JP | 2005-008765 A | 1/2005 |
| JP | 2005-029527 A | 2/2005 |
| JP | 2005-29539 A | 2/2005 |
| JP | 2005-084365 A | 3/2005 |
| JP | 2005-266766 A | 9/2005 |
| WO | 2004-074242 A2 | 9/2004 |

OTHER PUBLICATIONS

\* cited by examiner

SULFONATE SALTS AND DERIVATIVES, PHOTOACID GENERATORS, RESIST COMPOSITIONS, AND PATTERNING PROCESS

CROSS-REFERENCE TO RELATED APPLICATION

This application is a divisional application of U.S. Ser. No. 11/767,783, filed Jun. 25, 2007, which claims priority under 35 U.S.C. §119(a) on Patent Application No. 2006-176044 filed in Japan on Jun. 27, 2006, the entire contents of which are hereby incorporated by reference.

TECHNICAL FIELD

This invention relates to photoacid generators, resist compositions comprising the same, and a patterning process using the same. More particularly, it relates to novel sulfonate salts and derivatives thereof suitable for use as photoacid generators for resist compositions.

BACKGROUND OF THE INVENTION

While a number of recent efforts are being made to achieve a finer pattern rule in the drive for higher integration and operating speeds in LSI devices, DUV and VUV lithography is thought to hold particular promise as the next generation in microfabrication technology. In particular, photolithography using an ArF excimer laser as the light source is thought requisite to the micropatterning technique capable of achieving a feature size of 0.13 µm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerin) between the projection lens and the wafer, allowing the projection lens to be designed to a numerical aperture (NA) of 1.0 or higher and achieving a higher resolution. See Journal of Photopolymer Science and Technology, Vol. 17, No. 4, p 587 (2004).

In the photolithography using an ArF excimer laser (wavelength 193 nm) as the light source, a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polyacrylic acid and derivatives thereof, norbornene-maleic anhydride alternating copolymers, polynorbornene, ring-opening metathesis polymers, and hydrogenated ring-opening metathesis polymers have been proposed as the base resin. This choice is effective to some extent in that the transparency of a resin alone is increased.

Studies have also been made on photoacid generators. In prior art chemically amplified resist compositions for lithography using KrF excimer laser, photoacid generators capable of generating alkane- or arene-sulfonic acid are used. However, the use of these photoacid generators in chemically amplified resist compositions for ArF lithography results in an insufficient acid strength to scissor acid labile groups on the resin, a failure of resolution or a low sensitivity. Thus these photoacid generators are not suited for the fabrication of microelectronic devices.

For the above reason, photoacid generators capable of generating perfluoroalkanesulfonic acid having a high acid strength are generally used in ArF chemically amplified resist compositions. These photoacid generators capable of generating perfluoroalkanesulfonic acid have already been developed for use in the KrF resist compositions. For instance, JP-A 2000-122296 and U.S. Pat. No. 6,048,672 (or JP-A 11-282168) describe photoacid generators capable of generating perfluorohexanesulfonic acid, perfluorooctanesulfonic acid, perfluoro-4-ethylcyclohexanesulfonic acid, and perfluorobutanesulfonic acid. JP-A 2002-214774, US Patent Application Publication 2003-0113659 A1 (JP-A 2003-140332), and US Patent Application Publication 2002-0197558 A1 describe novel photoacid generators capable of generating perfluoroalkyl ether sulfonic acids.

On the other hand, perfluorooctanesulfonic acid and homologues thereof (collectively referred to as PFOS) are considered problematic with respect to their stability (or non-degradability) due to C—F bonds, and biological concentration and accumulation due to hydrophobic and lipophilic natures. The US EPA adopted Significant New Use Rule, listing 13 PFOS-related chemical substances and further listing 75 chemical substances although their use in the photoresist field is excluded. See Federal Register/Vol. 67, No. 47, page 11008/Monday, Mar. 11, 2002, and Federal Register/Vol. 67, No. 236, page 72854/Monday, Dec. 9, 2002.

Facing the PFOS-related problems, manufacturers made efforts to develop partially fluorinated alkane sulfonic acids having a reduced degree of fluorine substitution. For instance, JP-A 2004-531749 describes the development of α,α-difluoroalkanesulfonic acid salts from α,α-difluoroalkene and a sulfur compound and discloses a resist composition comprising a photoacid generator which generates such sulfonic acid upon irradiation, specifically di(4-tert-butylphenyl)iodonium 1,1-difluoro-2-(1-naphthyl)ethanesulfonate. JP-A 2004-2252 describes the development of α,α,β,β-tetrafluoroalkanesulfonic acid salts from α,α,β,β-tetrafluoro-α-iodoalkane and sulfur compound and discloses a photoacid generator capable of generating such a sulfonic acid and a resist composition comprising the same. JP-A 2004-307387 discloses 2-(bicyclo[2.2.1]hept-2-yl)-1,1-difluoroethanesulfonic acid salts and a method of preparing the same. Furthermore, JP-A 2005-266766 discloses a photosensitive composition comprising a compound capable of generating a partially fluorinated alkane sulfonic acid having a sulfonylamide structure derived from perfluoroalkylene disulfonyl difluoride.

The substances disclosed in these patents have a reduced degree of fluorine substitution, but suffer from several problems. They are less degradable because they are based on substantially undegradable hydrocarbon skeletons and they do not possess readily degradable substituent groups such as ester groups. A certain limit is imposed on the molecular design for changing the size of alkanesulfonic acid. The starting materials containing fluorine are expensive.

With respect to the immersion lithography, there remain some problems. Minute water droplets are left on the resist and wafer after the immersion exposure, which can often cause damages and defects to the resist pattern profile. The resist pattern after development can collapse or deform into a T-top profile. There exists a need for a patterning process which can form a satisfactory resist pattern after development according to the immersion lithography.

DISCLOSURE OF THE INVENTION

The photoacid generator (PAG) produces an acid which must satisfy many requirements including a sufficient acid strength to cleave acid labile groups in a resist material, stability in the resist material during shelf storage, an adequate diffusion in the resist material, low volatility, minimal dissolution in water, no foreign matter left after development and resist removal, and good degradability in that it is decomposed away after the expiration of its role in lithography without imposing a load to the environment. No acids produced by prior art PAGs satisfy these requirements.

An object of the invention is to solve the problems of prior art photoacid generators, and to provide sulfonate salts and derivatives thereof which are effective in the ArF immersion lithography due to minimized dissolution in water and controlled formation of foreign matter inherent to the immersion lithography, and are thus suitable as a raw material for photoacid generator or a photoacid generator in resist material. Another object is to provide a photoacid generator, a resist composition, and a patterning process.

The inventors have found that 4-acyloxy-1,1,2,2-tetrafluorobutanesulfonic acid salts are prepared by starting with 1,4-dibromo-1,1,2,2-tetrafluorobutane or 4-bromo-3,3,4,4-tetrafluoro-1-butene which is readily available in the industry, deriving therefrom a 4-bromo-3,3,4,4-tetrafluorobutyl ester of aliphatic or aromatic carboxylic acid, and reacting the ester with a sulfinic agent such as sodium dithionite, followed by oxidation into a sulfonic acid; that once compounds, typically onium salts, oxime sulfonates and sulfonyloxyimides are prepared from these sulfonate salts, ester hydrolysis is performed to form compounds which are effective photoacid generators in chemically amplified resist compositions. The present invention is predicated on this finding.

The present invention provides sulfonate salts, derivatives thereof, photoacid generators, resist compositions and a patterning process, defined below.

[1] A sulfonate salt having the general formula (1).

$$HOCH_2CH_2CF_2CF_2SO_3^- M^+ \quad (1)$$

Herein $M^+$ is a lithium, sodium, potassium, ammonium, or tetramethylammonium ion.

[2] A photoacid generator for chemically amplified resist compositions which generates a sulfonic acid having the general formula (1a) upon exposure to high-energy radiation selected from UV, deep-UV, electron beam, x-ray, excimer laser, gamma-ray and synchrotron radiation.

$$HOCH_2CH_2CF_2CF_2SO_3^- H^+ \quad (1a)$$

[3] A sulfonium salt having the general formula (2).

(2)

Herein $R^1$, $R^2$ and $R^3$ are each independently selected from the class consisting of substituted or unsubstituted, straight or branched $C_1$-$C_{10}$ alkyl, alkenyl and oxoalkyl groups, and substituted or unsubstituted $C_6$-$C_{18}$ aryl, aralkyl and aryloxoalkyl groups, or any two or more of $R^1$, $R^2$ and $R^3$ may bond together to form a ring with the sulfur atom.

[4] A sulfonium salt having the general formula (2a).

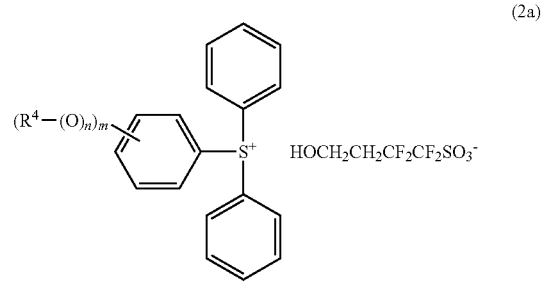
(2a)

Herein $R^4$ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, and n is 0 or 1.

[5] A iodonium salt having the general formula (2b).

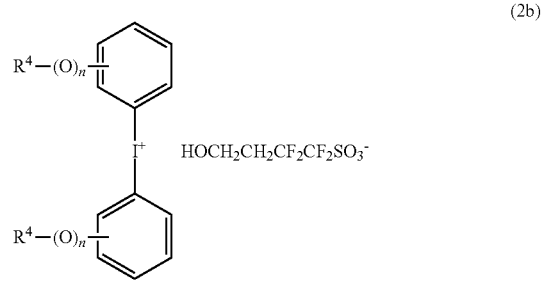
(2b)

Herein $R^4$ is a substituted or unsubstituted, straight, branched or cyclic $C_1$-$C_{20}$ alkyl or alkenyl group or a substituted or unsubstituted $C_6$-$C_{14}$ aryl group, and n is 0 or 1.

[6] A N-sulfonyloxyimide compound having the general formula (3a).

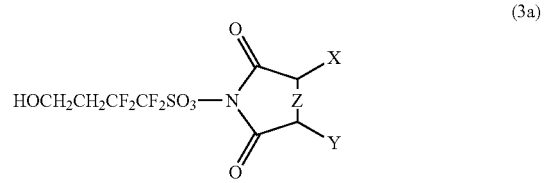
(3a)

Herein X and Y are each independently hydrogen or a substituted or unsubstituted $C_1$-$C_6$ alkyl group, or X and Y may bond together to form a saturated or unsaturated $C_6$-$C_{12}$ ring with the carbon atoms to which they are attached, and Z is a single bond, double bond, methylene group or oxygen atom.

[7] An oxime sulfonate compound having the general formula (3b).

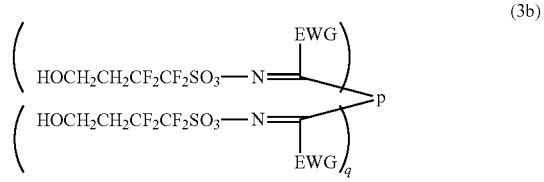
(3b)

Herein q is 0 or 1; when q is 0, p is a single bond, a substituted or unsubstituted $C_1$-$C_{20}$ alkyl group or a substituted or unsubstituted $C_6$-$C_{15}$ aryl group; when q is 1, p is a substituted or unsubstituted $C_1$-$C_{20}$ alkylene group or a substituted or unsubstituted $C_6$-$C_{15}$ arylene group; EWG is a cyano, trifluoromethyl, perfluoroethyl, perfluoropropyl, 5H-perfluoropentyl, 6H-perfluorohexyl, nitro or methyl group, and when q is 1, two EWG's may bond together to form a ring of 6 carbon atoms with the carbon atoms to which they are attached.

[8] A resist composition comprising a base resin, an acid generator, and an organic solvent, said acid generator comprising a photoacid generator which generates a sulfonic acid having formula (1a) as set forth in [2].

[9] The resist composition of [8], wherein said base resin is at least one polymer selected from the group consisting of poly (meth)acrylic acid and derivatives thereof, alternating copolymers of a cycloolefin derivative and maleic anhydride, copolymers of ternary or more components comprising a cycloolefin derivative, maleic anhydride, and polyacrylic acid or derivatives thereof, cycloolefin derivative/α-trifluoromethyl acrylate derivative copolymers, polynorbornene, ring-opening metathesis polymers, and hydrogenated ring-opening metathesis polymers.

[10] The resist composition of [8], wherein said base resin is a polymeric structure containing silicon atoms.

[11] The resist composition of [8], wherein said base resin is a polymeric structure containing fluorine atoms.

[12] A chemically amplified positive resist composition comprising a base resin as set forth in [9], [10] or [11], a photoacid generator which generates a sulfonic acid having formula (1a) as set forth in [2], and a solvent, wherein said base resin is insoluble or substantially insoluble in a liquid developer, and becomes soluble under the action of the acid.

[13] The chemically amplified positive resist composition of [12], further comprising a quencher.

[14] The chemically amplified positive resist composition of [12] or [13], further comprising a dissolution inhibitor.

[15] A process for forming a pattern comprising the steps of applying the resist composition of any one of [8] to [14] onto a substrate to form a coating; heat treating the coating and exposing it to high-energy radiation having a wavelength of up to 300 nm through a photomask; and optionally heat treating and developing the exposed coating with a developer.

[16] The process of [15], wherein the exposing step relies on immersion lithography comprising directing radiation from an ArF excimer laser having a wavelength of 193 nm through a projection lens, with a liquid such as water, glycerin or ethylene glycol intervening between the coated substrate and the projection lens.

BENEFITS OF THE INVENTION

The sulfonic acids of the invention exhibit a high acidity, despite a low degree of fluorine substitution within a molecule, due to fluorine substitution solely at α- and β-positions. The distance of acid diffusion can be restrained as appropriate by hydrogen bonds or the like due to the inclusion of hydroxyl groups within a molecule. In addition, the sulfonic acids are useful as synthesis intermediates having a wide spectrum of molecular design because various substituent groups such as acyl and alkyl groups can be readily introduced by reaction with acid halides, acid anhydrides or alkyl halides. The photoacid generators that generate these sulfonic acids perform well without raising problems during the device fabrication process including coating, pre-baking, exposure, post-exposure baking, and developing steps. Because of a low molecular weight and inclusion of hydrophilic groups, these compounds are less accumulative in the human body. In the disposal by combustion, the compounds are more combustible because of a low degree of fluorine substitution.

DESCRIPTION OF THE PREFERRED EMBODIMENTS

Figure 1:
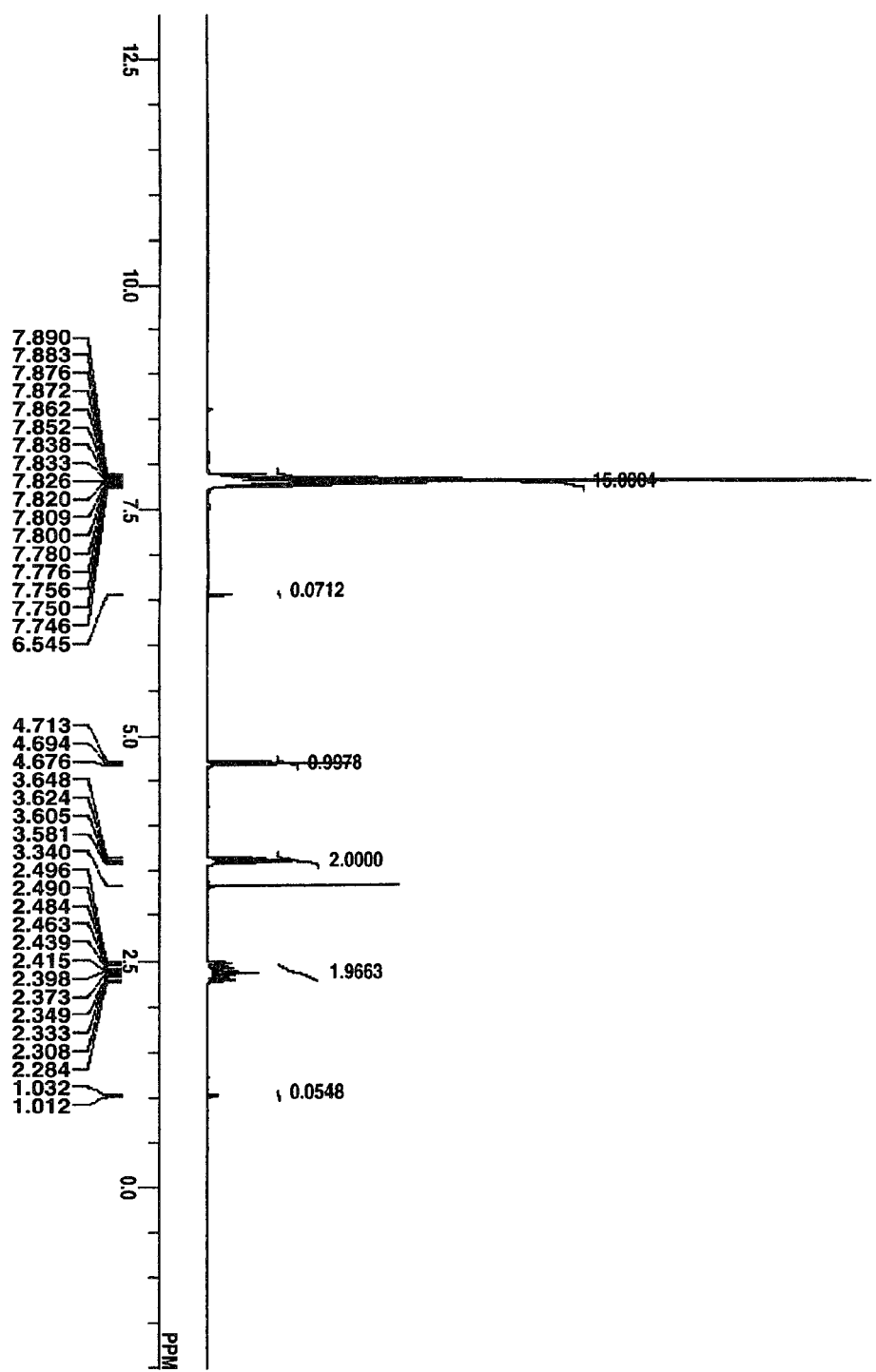
FIG. 1 is a diagram showing the $^1$H-NMR/DMSO-$d_6$ spectrum of PAG1 in Synthesis Example 10.

The notation (Cn-Cm) means a group containing from n to m carbon atoms per group.

Sulfonate Salt

The sulfonate salt of the invention has the general formula (1):

$$HOCH_2CH_2CF_2CF_2SO_3^- M^+ \quad (1)$$

wherein $M^+$ is a lithium, sodium, potassium, ammonium, or tetramethylammonium ion.

For simplicity of synthesis and ease of isolation of sulfonate salts, only lithium, sodium, potassium, ammonium and tetramethylammonium ions are specified herein as $M^+$. Nevertheless, divalent cations like calcium and magnesium ions and other organic ammonium ions are also acceptable. No particular limit is imposed on sulfonate salts as long as they can exist as stable salts.

Photoacid Generator

The photoacid generators of the invention are compounds derived from the sulfonate salts having formula (1), typically sulfonium salts, iodonium salts, oxime sulfonates and sulfonyloxyimides. These compounds are sensitive to high-energy radiation such as UV, deep-UV, electron beam, x-ray, excimer laser, gamma-ray and synchrotron radiation and generate sulfonic acids having the general formula (1a) so that they are useful as photoacid generators in chemically amplified resist compositions.

$$HOCH_2CH_2CF_2CF_2SO_3^- H^+ \quad (1a).$$

Sulfonium Salt

The sulfonium salt of the invention has the general formula (2):

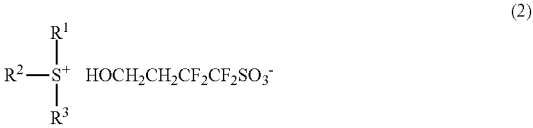

(2)

wherein $R^1$, $R^2$ and $R^3$ are each independently a substituted or unsubstituted, straight or branched $C_1$-$C_{10}$ alkyl, alkenyl or oxoalkyl group, or a substituted or unsubstituted $C_6$-$C_{18}$ aryl, aralkyl or aryloxoalkyl group, or any two or more of $R^1$, $R^2$ and $R^3$ may bond together to form a ring with the sulfur atom.

In formula (2), $R^1$, $R^2$ and $R^3$ are each independently selected from among substituted or unsubstituted, straight or branched $C_1$-$C_{10}$ alkyl, alkenyl and oxoalkyl groups, and substituted or unsubstituted $C_6$-$C_{18}$ aryl, aralkyl and aryloxoalkyl groups, or any two or more of $R^1$, $R^2$ and $R^3$ may bond together to form a ring with the sulfur atom. Suitable alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include vinyl, allyl, propenyl, butenyl, hexenyl, and cyclohexenyl. Suitable oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include phenyl, naphthyl, and thienyl; 4-hydroxyphenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include benzyl, 1-phenylethyl and 2-phenylethyl. Suitable aryloxoalkyl groups include 2-aryl-2-oxoethyl groups such as 2-phenyl-2-oxoethyl, 2-(1-naphthyl)-2-oxoethyl, and 2-(2-naphthyl)-2-oxoethyl. When two or more of $R^1$, $R^2$ and $R^3$ bond together to form a ring structure with the sulfur atom, 1,4-butylene and 3-oxa-1,5-pentylene are exemplary of each. Also included are aryl groups having polymerizable substituent radicals such as acryloyloxy and methacryloyloxy radicals, examples of which are 4-acryloyloxyphenyl, 4-methacryloyloxyphenyl, 4-acryloyloxy-3,5-dimethylphenyl, 4-methacryloyloxy-3,5-dimethylphenyl, 4-vinyloxyphenyl, and 4-vinylphenyl groups.

Illustrative examples of the sulfonium cation include triphenylsulfonium, 4-hydroxyphenyldiphenylsulfonium, bis(4-hydroxyphenyl)phenylsulfonium, tris(4-hydroxyphenyl)sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxyphenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. Preferred cations are triphenylsulfonium, 4-tert-butylphenyldiphenylsulfonium, 4-tert-butoxyphenyldiphenylsulfonium, tris(4-tert-butylphenyl)sulfonium, and 4-tert-butoxycarbonylmethyloxyphenyldiphenylsulfonium.

Also included are 4-methacryloyloxyphenyldiphenylsulfonium, 4-acryloyloxyphenyldiphenylsulfonium, 4-methacryloyloxyphenyldimethylsulfonium, 4-acryloyloxyphenyldimethylsulfonium, (4-methacryloyloxy-3,5-dimethylphenyl)diphenylsulfonium, (4-acryloyloxy-3,5-dimethylphenyl)diphenylsulfonium, and the like. For these polymerizable sulfonium cations, reference may be made to JP-A 4-230645 and JP-A 2005-84365. These polymerizable sulfonium salts may be used as a monomer in forming a polymer to be described later.

Another embodiment is a sulfonium salt having the general formula (2a):

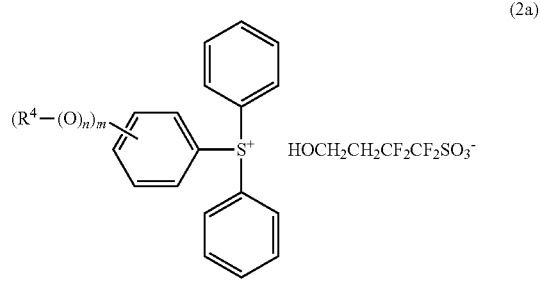

(2a)

wherein $R^4$ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, and n is 0 or 1.

In formula (2a), the substitution position of $R^4$—$(O)_n$— group is not particularly limited, but is preferably 4- or 3-position on the phenyl group, and more preferably 4-position. Examples of groups represented by $R^4$ include methyl, ethyl, n-propyl, sec-propyl, cyclopropyl, n-butyl, sec-butyl, isobutyl, tert-butyl, n-pentyl, cyclopentyl, n-hexyl, cyclohexyl, n-octyl, n-decyl, n-dodecyl, trifluoromethyl, phenyl, 4-methoxyphenyl, and 4-tert-butylphenyl. In the case of n=1, acryloyl, methacryloyl, vinyl, and allyl are exemplary of $R^4$. The letter m is an integer of 1 to 5, and preferably 1, and n is 0 or 1.

Illustrative examples of the sulfonium cation include 4-methylphenyldiphenylsulfonium, 4-ethylphenyldiphenylsulfonium, 4-tert-butylphenyldiphenylsulfonium, 4-cyclohexylphenyldiphenylsulfonium, 4-n-hexylphenyldiphenylsulfonium, 4-n-octylphenyldiphenylsulfonium, 4-methoxyphenyldiphenylsulfonium, 4-ethoxyphenyldiphenylsulfonium, 4-tert-butoxyphenyldiphenylsulfonium, 4-cyclohexyloxyphenyldiphenylsulfonium, 4-n-hexyloxyphenyldiphenylsulfonium, 4-n-octyloxyphenyldiphenylsulfonium, 4-dodecyloxyphenyldiphenylsulfonium, 4-trifluoromethylphenyldiphenylsulfonium, 4-trifluoromethyloxyphenyldiphenylsulfonium, 4-tert-butoxycarbonylmethyloxyphenyldiphenylsulfonium, 4-methacryloyloxyphenyldiphenylsulfonium, 4-acryloyloxyphenyldiphenylsulfonium, 4-methacryloyloxyphenyldimethylsulfonium, 4-acryloyloxyphenyldimethylsulfonium, (4-n-hexyloxy-3,5-dimethylphenyl)diphenylsulfonium, (4-methacryloyloxy-3,5-dimethylphenyl)diphenylsulfonium, and (4-acryloyloxy-3,5-dimethylphenyl)diphenylsulfonium.

Iodonium Salt

A further embodiment of the invention is a iodonium salt having the general formula (2b):

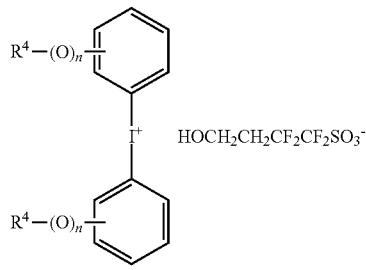

(2b)

wherein $R^4$ is a substituted or unsubstituted, straight, branched or cyclic $C_1$-$C_{20}$ alkyl or alkenyl group or a substituted or unsubstituted $C_6$-$C_{14}$ aryl group, and n is 0 or 1.

In formula (2b), $R^4$ and n are as defined above. The substitution position of $R^4$—$(O)_n$— group is not particularly limited, but is preferably 4- or 3-position on the phenyl group, and more preferably 4-position.

Illustrative examples of the iodonium cation include bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, and 4-methacryloyloxyphenylphenyliodonium,
with the bis(4-tert-butylphenyl)iodonium being preferred.

N-Sulfonyloxyimide

A further embodiment of the invention is a N-sulfonyloxyimide compound having the general formula (3a):

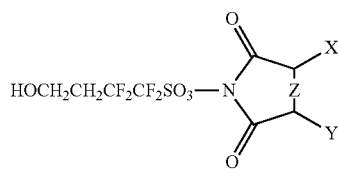

(3a)

wherein X and Y are each independently hydrogen or a substituted or unsubstituted $C_1$-$C_6$ alkyl group, or X and Y may bond together to form a saturated or unsaturated $C_6$-$C_{12}$ ring with the carbon atoms to which they are attached, and Z is a single bond, double bond, methylene group or oxygen atom.

Illustrative examples of the imide skeleton excluding the sulfonate moiety are given below. For the imide skeleton, reference may be made to JP-A 2003-252855.

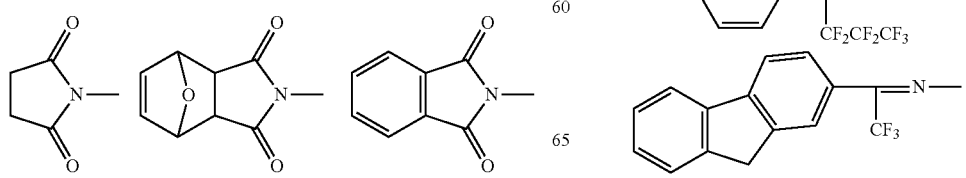

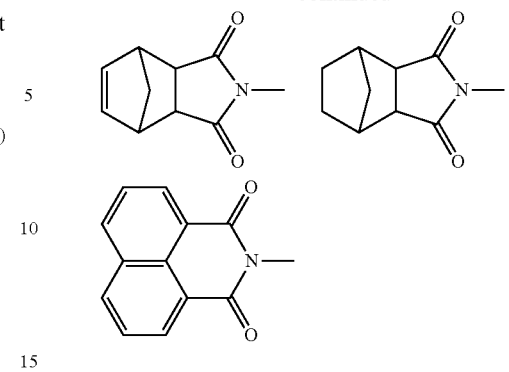

Oxime Sulfonate

A further embodiment of the invention is an oxime sulfonate compound having the general formula (3b):

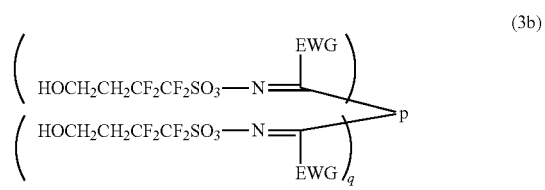

(3b)

wherein q is 0 or 1. When q is 0, p is a single bond, a substituted or unsubstituted $C_1$-$C_{20}$ alkyl group or a substituted or unsubstituted $C_6$-$C_{15}$ aryl group. When q is 1, p is a substituted or unsubstituted $C_1$-$C_{20}$ alkylene group or a substituted or unsubstituted $C_6$-$C_{15}$ arylene group. EWG is a cyano, trifluoromethyl, perfluoroethyl, perfluoropropyl, 5H-perfluoropentyl, 6H-perfluorohexyl, nitro or methyl group. When q is 1, two EWG's may bond together to form a ring of 6 carbon atoms with the carbon atoms to which they are attached.

The skeletons of the oxime sulfonates are described in U.S. Pat. No. 6,261,738, JP-A 9-95479, JP-A 9-208554, JP-A 9-230588, Japanese Patent No. 2,906,999, JP-A 9-301948, JP-A 2000-314956, JP-A 2001-233842, and International Publication 2004-074242.

Exemplary skeletons of oxime sulfonates excluding the sulfonate moiety are given below.

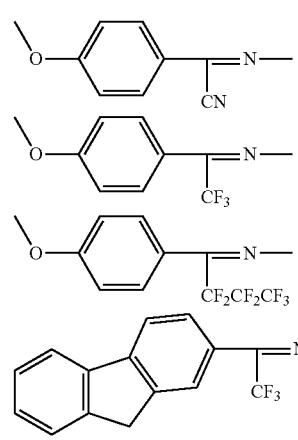

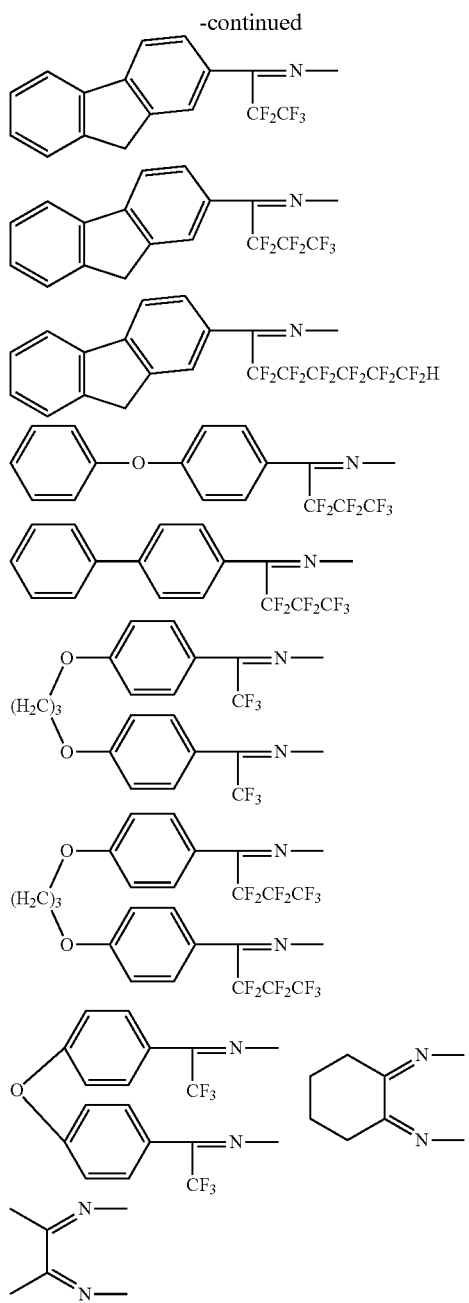

Described below is how to synthesize the sulfonium salts, iodonium salts, oxime sulfonates or sulfonyloxyimides which generate sulfonic acids having formula (1a).

Synthesis may be carried out by starting with 1,4-dibromo-1,1,2,2-tetrafluorobutane which is readily available in the industry, subjecting it to selective substitution reaction with a carboxylic acid salt such as sodium carboxylate or ammonium carboxylate to derive a 4-bromo-3,3,4,4-tetrafluorobutyl ester of aliphatic or aromatic carboxylic acid, and reacting the ester with a sulfonic agent such as sodium dithionite in the presence of a base such as sodium hydrogen carbonate in a solvent such as water, acetonitrile or a mixture thereof, and customarily oxidizing the product with an oxidizing agent such as hydrogen peroxide in the presence of sodium tungstate in water as a solvent, thereby synthesizing a 4-acyloxy-1,1,2,2-tetrafluorobutanesulfonic acid salt.

From the aforementioned sulfonic acid salts and onium salts, sulfonium or iodonium salts can be synthesized by a standard anion exchange technique. The onium salts can be synthesized in accordance with the teachings of The Chemistry of Sulfonium Group Part 1, John-Wiley & Sons (1981), Advanced Photochemistry, Vol. 17, John-Wiley & Sons (1992), J. Org. Chem., 53, 5571-5573, 1988, JP-A 8-311018, JP-A 9-15848, JP-A 2001-122850, JP-A 7-25846, JP-A 2001-181221, JP-A 2002-193887, and JP-A 2002-193925. The onium cation having an acryloyloxy or methacryloyloxy group as the polymerizable substituent group can be synthesized by reacting (currently available) hydroxyphenyldiphenylsulfonium halide with acryloyl chloride or methacryloyl chloride under basic conditions according to the methods described in JP-A 4-230645 and JP-A 2005-84365.

Anion exchange may be performed in an alcohol solvent such as methanol or ethanol or a two-layer system of dichloromethane and water or the like. Alternatively, anion exchange may be performed by another recipe of reacting a corresponding methyl sulfonate with sulfonyl halide or iodonium halide, and removing the halide ion as methyl halide, as taught in JP-A 2002-167340.

Also, imide sulfonates or oxime sulfonates can be synthesized by reacting the sulfonate salt with a chlorinating agent such as thionyl chloride, phosphorus oxychloride or phosphorus pentachloride to form a corresponding sulfonyl chloride or sulfonic acid anhydride, and further reacting with N-hydroxydicarboxylimide or oxime in an ordinary manner. For the synthesis of imide sulfonate or oxime sulfonate, reference should be made to the above-cited JP-A 2003-252855, U.S. Pat. No. 6,261,738, JP-A 9-95479, JP-A 9-208554, JP-A 9-230588, Japanese Patent No. 2,906,999, JP-A 9-301948, JP-A 2000-314956, JP-A 2001-233842, and International Publication 2004/074242.

Alternatively, sulfonium salts, iodonium salts, imide sulfonate and oxime sulfonate compounds of formula (2), (2a), (2b), (3a) or (3b) can be synthesized by subjecting the aforementioned sulfonium salts, iodonium salts, imide sulfonates or oxime sulfonates to hydrolysis or solvolysis in an ordinary manner in the presence of a base such as sodium hydroxide in a solvent mixture of water and alcohol or acetone.

Further, the compound of formula (1) can be synthesized by hydrolyzing the 4-acyloxy-1,1,2,2-tetrafluorosulfonic acid salt in water in the presence of a base such as sodium hydroxide or tetrabutylammonium hydroxide. The formation of the product may be confirmed by $^{19}F$ nuclear magnetic resonance spectroscopy ($^{19}F$-NMR) or time-of-flight mass spectrometry (TOFMS). The product may be subjected to anion exchange by a standard technique, thereby synthesizing the compound of formula (2), (2a) or (2b).

Also, the sulfonic acid salt of formula (1) can be synthesized by starting with 4-bromo-3,3,4,4-tetrafluoro-1-butene which is readily available in the industry, effecting hydroboration with a borane such as 9-borabicyclo[3.3.1]nonane (9-BBN) in a solvent such as n-hexane or tetrahydrofuran by a standard technique, treating the product with an oxidizing agent such as aqueous hydrogen peroxide in the presence of a base such as sodium hydroxide to form 4-bromo-3,3,4,4-tetrafluoro-1-butanol, followed by conversion into a sulfonic acid form and subsequently into a sulfonic acid form.

Notably, from the sulfonate salt of formula (1) or the sulfonate of formula (2), (2a), (2b), (3a) or (3b) obtained by the aforementioned processes, a photoacid generator in the form of a sulfonate salt or sulfonium salt, iodonium salt, imide sulfonate or oxime sulfonate having a carboxylic acid ester, sulfonic acid ester or ether structure within the molecule can be obtained by reaction with a carboxylic halide or carboxylic anhydride, sulfonic halide or alkyl halide in the presence of a base such as triethylamine in a solvent such as methylene chloride.

Also, from the sulfonate salt of formula (1) or the compound of formula (2), (2a), (2b), (3a) or (3b), a photoacid generator having a carboxylic acid ester structure can be obtained by reaction with an aliphatic or aromatic carboxylic halide or aliphatic or aromatic carboxylic anhydride. When a difunctional carboxylic acid halide or acid anhydride is used instead, a difunctional sulfonic acid or derivative thereof can be synthesized.

As described above, a first embodiment of the present invention provides a sulfonate salt having formula (1). A second embodiment of the present invention provides a photoacid generator for chemically amplified resist compositions which generates a sulfonic acid having formula (1a) upon exposure to high-energy radiation. A third embodiment of the present invention provides a sulfonium salt, iodonium salt, dicarboxylimide sulfonate, and oxime sulfonate serving as photoacid generators in chemically amplified resist compositions. A fourth embodiment of the present invention provides a resist composition comprising a photoacid generator which generates a sulfonic acid having formula (1a) upon exposure to high-energy radiation and a resin which changes its solubility in an alkaline developer liquid under the action of acid.

Resist Composition

The resist composition of the invention is typically embodied as (i) a chemically amplified positive resist composition comprising (A) a photoacid generator which generates a sulfonic acid having formula (1a), (B) an organic solvent, (C) a base resin which changes its solubility in an alkaline developer liquid under the action of acid, and one or more optional components including (D) a quencher, (E) a photoacid generator other than (A), (F) an organic acid derivative and/or fluorinated alcohol, and (G) a dissolution inhibitor having a molecular weight of up to 3,000; and (ii) a chemically amplified negative resist composition comprising (A) a photoacid generator which generates a sulfonic acid having formula (1a), (B) an organic solvent, (C') a base resin which is normally alkali soluble, but becomes substantially alkali insoluble under the action of a crosslinker, (H) a crosslinker which induces crosslinkage under the action of acid, and one or more optional components including (D) a quencher and (E) a photoacid generator other than (A).

The PAG which generates a sulfonic acid having formula (1a) as component (A) is as described above. More specifically, it is a compound having formula (2), (2a), (2b), (3a) or (3b). In the resist composition, the PAG is compounded in an amount of 0.1 to 10 parts, more preferably 1 to 7 parts by weight per 100 parts by weight of the base resin.

Component B

The organic solvent used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof.

Of the above organic solvents, it is recommended to use diethylene glycol dimethyl ether, 1-ethoxy-2-propanol, propylene glycol monomethyl ether acetate (PGMEA), cyclohexanone and mixtures thereof because the photoacid generator is most soluble therein.

An appropriate amount of the organic solvent used is about 200 to 3,000 parts, especially about 400 to 2,000 parts by weight per 100 parts by weight of the base resin.

Component C

The base resins used as component (C) or (C') in the inventive compositions include polyhydroxystyrene (PHS), and copolymers of PHS with styrene, (meth)acrylic acid esters or other polymerizable olefinic compounds, for KrF excimer laser resist use; (meth)acrylic acid ester polymers, alternating copolymers of cycloolefin with maleic anhydride, copolymers further containing vinyl ethers or (meth)acrylic acid esters, polynorbornene, ring-opening metathesis polymerized cycloolefins, and hydrogenated ring-opening metathesis polymerized cycloolefins, for ArF excimer laser resist use; and fluorinated forms of the foregoing polymers (for both KrF and ArF laser uses) for $F_2$ excimer laser resist use, although the base resins are not limited to these polymers. Understandably, the sulfonium salts and iodonium salts having polymerizable substituent groups according to the invention may be used as a monomer component in forming the base resin. Typical sulfonium and iodonium salts for such use are combinations of onium cations such as (4-acryloyloxyphenyl)diphenylsulfonium, (4-methacryloyloxyphenyl)diphenylsulfonium, (4-acryloyloxyphenyl)phenyliodonium, and (4-methacryloyloxyphenyl)phenyliodonium cations with anions such as 1,1,2,2-tetrafluoro-4-hydroxybutanesulfonate. The base resins may be used alone or in admixture of two or more. In the case of positive resist compositions, it is a common practice to substitute acid labile groups for hydroxyl groups on phenol, carboxyl groups or fluorinated alkyl alcohols for reducing the rate of dissolution in unexposed regions.

The base resins are not limited to the foregoing resins. Use may also be made of the resins described in the following patents.

| | |
|---|---|
| JP-A 2000-159758 | JP-A 2000-186118 |
| JP-A 2000-309611 | JP-A 2000-327633 |
| JP-A 2000-330283 | JP-A 2001-329052 |
| JP-A 2002-202609 | JP-A 2002-161116 |
| JP-A 2003-2883 | JP-A 2003-20313 |
| JP-A 2003-26728 | JP-A 2003-34706 |
| JP-A 2003-64134 | JP-A 2003-66612 |
| JP-A 2003-113213 | JP-A 2003-316027 |
| JP-A 2003-321466 | JP-A 2004-143153 |
| JP-A 2004-124082 | JP-A 2004-115486 |
| JP-A 2004-62175 | |

In a preferred embodiment, the base resin is at least one polymer selected from among poly(meth)acrylic acid and derivatives thereof, alternating copolymers of a cycloolefin derivative and maleic anhydride, copolymers of three or more components comprising a cycloolefin derivative, maleic anhydride, and polyacrylic acid or derivatives thereof, cycloolefin derivative-α-trifluoromethyl acrylate derivative copolymers, polynorbornene, ring-opening metathesis polymers, and hydrogenated ring-opening metathesis polymers.

In another preferred embodiment, the base resin is a polymeric structure containing silicon atoms or a polymeric structure containing fluorine atoms. Such polymers include those described in the following patents.

| | |
|---|---|
| JP-A 2005-8765 | JP-A 2004-354417 |
| JP-A 2004-352743 | JP-A 2004-331854 |
| JP-A 2004-331853 | JP-A 2004-292781 |
| JP-A 2004-252405 | JP-A 2004-190036 |
| JP-A 2004-115762 | JP-A 2004-83873 |
| JP-A 2004-59844 | JP-A 2004-35671 |
| JP-A 2004-83900 | JP-A 2004-99689 |
| JP-A 2004-145048 | JP-A 2004-217533 |
| JP-A 2004-231815 | JP-A 2004-244439 |
| JP-A 2004-256562 | JP-A 2004-307447 |
| JP-A 2004-323422 | JP-A 2005-29527 |
| JP-A 2005-29539 | |

Included in the chemically amplified positive resist composition is a base resin having acid labile groups which is normally insoluble or substantially insoluble in developer, but becomes soluble in developer as a result of the acid labile groups being decomposed under the action of acid. The acid labile groups to be introduced into the base resin may be selected from a variety of such groups, preferably from $C_2$-$C_{30}$ acetal groups and tertiary $C_4$-$C_{30}$ alkyl groups having the formulae (C1) and (C2), respectively.

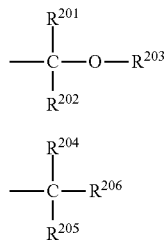

In formulae (C1) and (C2), $R^{201}$ and $R^{202}$ each are hydrogen or a straight, branched or cyclic $C_1$-$C_{20}$ alkyl group, which may contain a hetero atom such as oxygen, sulfur, nitrogen or fluorine, $R^{203}$, $R^{204}$, $R^{205}$ and $R^{206}$ each are a straight, branched or cyclic $C_1$-$C_{20}$ alkyl group, a $C_6$-$C_{10}$ aryl group or a $C_7$-$C_{10}$ aralkyl group, which may contain a hetero atom such as oxygen, sulfur, nitrogen or fluorine. A pair of $R^{201}$ and $R^{202}$, a pair of $R^{201}$ and $R^{203}$, a pair of $R^{202}$ and $R^{203}$, a pair of $R^{204}$ and $R^{205}$, a pair of $R^{204}$ and $R^{206}$, or a pair of $R^{205}$ and $R^{206}$, taken together, may form a ring of 3 to 30 carbon atoms with the carbon atom to which they are attached.

Illustrative examples of the acetal group of formula (C1) include, but are not limited to, methoxymethyl, ethoxymethyl, propoxymethyl, butoxymethyl, isopropoxymethyl, t-butoxymethyl, 1-methoxyethyl, 1-methoxypropyl, 1-methoxybutyl, 1-ethoxyethyl, 1-ethoxypropyl, 1-ethoxybutyl, 1-propoxyethyl, 1-propoxypropyl, 1-propoxybutyl, 1-cyclopentyloxyethyl, 1-cyclohexyloxyethyl, 2-methoxyisopropyl, 2-ethoxyisopropyl, 1-phenoxyethyl, 1-benzyloxyethyl, 1-phenoxypropyl, 1-benzyloxypropyl, 1-adamantyloxyethyl, 1-adamantyloxypropyl, 2-tetrahydrofuryl, 2-tetrahydro-2H-pyranyl, 1-(2-cyclohexanecarbonyloxyethoxy)ethyl, 1-(2-cyclohexanecarbonyloxyethoxy)propyl, 1-[2-(1-adamantylcarbonyloxy)ethoxy]ethyl, and 1-[2-(1-adamantylcarbonyloxy)ethoxy]propyl.

Illustrative examples of the tertiary alkyl group of formula (C2) include, but are not limited to, t-butyl, t-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

In the base resin, at least 1 mol % of hydrogen atoms of hydroxyl groups may be substituted by acid labile groups of the following general formula (C3a) or (C3b) for crosslinkage between molecules or within a molecule.

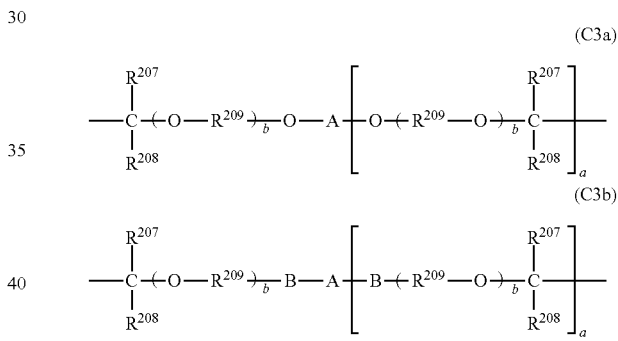

Herein, $R^{207}$ and $R^{208}$ each are hydrogen or a straight, branched or cyclic alkyl group of 1 to 8 carbon atoms, or $R^{207}$ and $R^{208}$, taken together, may form a ring, with the proviso that each of $R^{207}$ and $R^{208}$ is a straight or branched alkylene group of 1 to 8 carbon atoms when they form a ring. $R^{209}$ is a straight, branched or cyclic alkylene group of 1 to 10 carbon atoms. Letter "a" is an integer of 1 to 7 and "b" is 0 or an integer of 1 to 10. "A" is a (a+1)-valent aliphatic or alicyclic saturated hydrocarbon group, aromatic hydrocarbon group or heterocyclic group of 1 to 50 carbon atoms, which may have an intervening hetero atom and in which the hydrogen atom attached to a carbon atom may be partially replaced by a hydroxyl group, carboxyl group, carbonyl group or fluorine atom. B is —CO—O—, —NHCO—O— or —NHCONH—.

Illustrative examples of the crosslinking acetal linkages represented by formulae (C3a) and (C3b) are given below as (C3-1) through (C3-8), but not limited thereto.

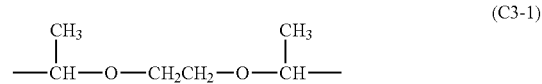

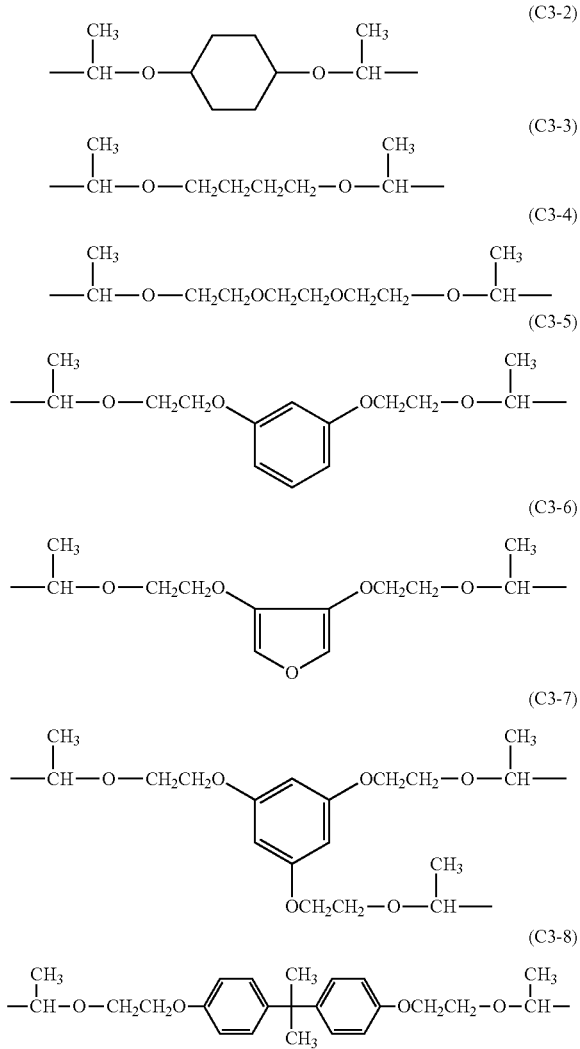

Preferably the base resin has a weight average molecular weight (Mw) of 2,000 to 100,000, as measured by gel permeation chromatography (GPC) versus polystyrene standards. With Mw below 2,000, film formation and resolution may become poor. With Mw beyond 100,000, resolution may become poor or foreign matter may generate during pattern formation.

In the base resin, the proportion of acid labile group-containing monomer units relative to the other monomer units (constituent units) is typically in a range of 10 to 70%, preferably 20 to 60%, in case intended for ArF excimer laser resist compositions; and typically in a range of 10 to 50%, preferably 20 to 40%, in case intended for KrF excimer laser resist compositions.

The monomer units other than the acid labile group-containing monomer units are preferably monomer units containing polar groups such as alcohols, fluorinated alcohols, ether, lactone, ester, acid anhydride, and carboxylic acid in the case of the base resins for ArF excimer laser resist compositions. The base resins for KrF excimer laser resist compositions may comprise units of styrene, indene and 4-acetoxystyrene in addition to 4-hydroxystyrene units having no acid labile groups incorporated. The monomer units to be incorporated may be of one type or of two or more different types.

Component D

The quencher used as component (D) is preferably a compound capable of suppressing the rate of diffusion when the acid generated by the photoacid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine Examples of suitable aromatic and heterocyclic amines include aniline derivatives (e.g., aniline, N-methylaniline, N-ethylaniline, N-propylaniline, N,N-dimethylaniline, N,N-bis(hydroxyethyl)aniline, 2-methylaniline, 3-methylaniline, 4-methylaniline, ethylaniline, propylaniline, dimethylaniline, 2,6-diisopropylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazane derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds with carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable nitrogen-containing compounds with sulfonyl group include 3-pyridinesulfonic acid and pyridinium p-toluenesulfonate. Examples of suitable nitrogen-containing compounds with hydroxyl group, nitrogen-containing compounds with hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl) pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide. Suitable carbamate derivatives include N-tert-butoxycarbonyl-N,N-dicyclohexylamine, N-tert-butoxycarbonylbenzimidazole, and oxazolidinone. Suitable ammonium salts include pyridinium p-toluenesulfonate, triethylammonium p-toluenesulfonate, trioctylammonium p-toluenesulfonate, triethylammonium 2,4,6-triisopropylbenzenesulfonate, trioctylammonium 2,4, 6-triisopropylbenzenesulfonate, triethylammonium camphorsulfonate, trioctylammonium camphorsulfonate, tetramethylammonium hydroxide, tetraethylammonium hydroxide, tetrabutylammonium hydroxide, benzyltrimethylammonium hydroxide, tetramethylammonium p-toluenesulfonate, tetrabutylammonium p-toluenesulfonate, benzyltrimethylammonium p-toluenesulfonate, tetramethylammonium camphorsulfonate, tetrabutylammonium camphorsulfonate, benzyltrimethylammonium camphorsulfonate, tetramethylammonium 2,4,6-triisopropylbenzenesulfonate, tetrabutylammonium 2,4,6-triisopropylbenzenesulfonate, benzyltrimethylammonium 2,4,6-triisopropylbenzenesulfonate, tetramethylammonium acetate, tetrabutylammonium acetate, benzyltrimethylammonium acetate, tetramethylammonium benzoate, tetrabutylammonium benzoate, and benzyltrimethylammonium benzoate.

In addition, amine compounds of the following general formula (Am-1) may also be included alone or in admixture.

$$N(Rx)_k(Ry)_{3-k} \quad (\text{Am-1})$$

In the formula, k is equal to 1, 2 or 3. The side chain Rx is independently selected from groups of the following general formulas (Rx-1) to (Rx-3). The side chain Ry is independently hydrogen or a straight, branched or cyclic $C_1$-$C_{20}$ alkyl group in which some or all hydrogen atoms may be substituted by fluorine atoms and which may contain an ether or hydroxyl group. Two or three Rx may bond together to form a ring.

$$-\!\!\!+\!R^{301}\!-\!O\!-\!R^{302}] \quad (\text{Rx-1})$$

$$-\!\!\!+\!R^{303}\!-\!O\!-\!R^{304}\!-\!\!\overset{\underset{\displaystyle O}{\|}}{C}\!-\!R^{305}\Big] \quad (\text{Rx-2})$$

$$-\!\!\!+\!R^{306}\!-\!\!\overset{\underset{\displaystyle O}{\|}}{C}\!-\!O\!-\!R^{307}\Big] \quad (\text{Rx-3})$$

In the formulas, $R^{301}$, $R^{303}$ and $R^{306}$ are independently straight or branched $C_1$-$C_4$ alkylene groups; $R^{302}$ and $R^{305}$ are independently hydrogen or straight, branched or cyclic $C_1$-$C_{20}$ alkyl groups in which some or all hydrogen atoms may be substituted by fluorine atoms and which may contain at least one hydroxyl group, ether group, ester group or lactone ring; $R^{304}$ is a single bond or a straight or branched $C_1$-$C_4$ alkylene group; $R^{307}$ is a straight, branched or cyclic $C_1$-$C_{20}$ alkyl group in which some or all hydrogen atoms may be substituted by fluorine atoms and which may contain at least one hydroxyl group, ether group, ester group or lactone ring.

Illustrative examples of the compounds of formula (Am-1) include, but are not limited to, tris(2-methoxymethoxyethyl) amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl) amine, tris(2-valeryloxyethyl)amine, tris(2-pivaloyloxyethyl)amine, N,N-bis(2-acetoxyethyl)-2-(acetoxyacetoxy) ethylamine, tris(2-methoxycarbonyloxyethyl)amine, tris(2-tert-butoxycarbonyloxyethyl)amine, tris[2-(2-oxopropoxy) ethyl]amine, tris[2-(methoxycarbonylmethyl)oxyethyl] amine, tris[2-(tert-butoxycarbonylmethyloxy)ethyl]amine, tris[2-(cyclohexyloxycarbonylmethyloxy)ethyl]amine, tris (2-methoxycarbonylethyl)amine, tris(2-ethoxycarbonylethyl)amine, N,N-bis(2-hydroxyethyl)-2-(methoxycarbonyl) ethylamine, N,N-bis(2-acetoxyethyl)-2-(methoxycarbonyl) ethylamine, N,N-bis(2-hydroxyethyl)-2-(ethoxycarbonyl) ethylamine, N,N-bis(2-acetoxyethyl)-2-(ethoxycarbonyl)

ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)ethylamine, N,N-bis(2-acetoxyethyl)-2-(tetrahydrofurfuryloxycarbonyl)ethylamine, N,N-bis(2-hydroxyethyl)-2-[2-oxotetrahydrofuran-3-yl)oxycarbonyl]ethylamine, N,N-bis(2-acetoxyethyl)-2-[2-oxotetrahydrofuran-3-yl)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more of cyclic structure-bearing amine compounds having the following general formula (Am-2).

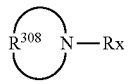

(Am-2)

Herein Rx is as defined above, and $R^{308}$ is a straight or branched $C_2$-$C_{20}$ alkylene group in which some or all hydrogen atoms may be substituted by fluorine atoms and which may contain one or more carbonyl, ether, ester or sulfide groups.

Illustrative examples of the cyclic structure-bearing amine compounds having formula (Am-2) include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-[2-(2-methoxyethoxy)ethoxy]ethylmorpholine, 2-[2-(2-butoxyethoxy)ethoxy]ethylmorpholine, 2-{2-[2-(2-methoxyethoxy)ethoxy]ethoxy}ethylmorpholine, 2-{2-[2-(2-butoxyethoxy)ethoxy]ethoxy}ethylmorpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, 2-methoxyethyl morpholinoacetate, 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl cyclohexanecarboxylate, and 2-morpholinoethyl adamantanecarboxylate.

Also, one or more of cyano-bearing amine compounds having the following general formulae (Am-3) to (Am-6) may be added.

(Am-3)

(Am-4)

(Am-5)

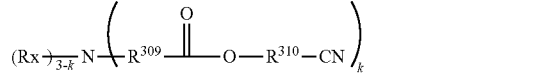

(Am-6)

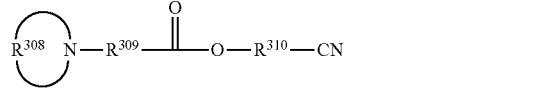

Herein, Rx, $R^{308}$ and k are as defined in formula (Am-1), and $R^{309}$ and $R^{310}$ each are independently a straight or branched $C_1$-$C_4$ alkylene group.

Illustrative examples of the cyano-bearing amine compounds having formulae (Am-3) to (Am-6) include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropionitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are amine compounds having an imidazole structure and a polar functional group, represented by the general formula (Am-7).

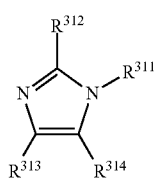
(Am-7)

Herein, $R^{311}$ is a straight, branched or cyclic $C_2$-$C_{20}$ alkyl group in which some or all hydrogen atoms may be substituted by fluorine atoms and which has one or more polar functional groups. The polar functional group is selected from among hydroxyl, carbonyl, ester, ether, sulfide, carbonate, cyano and acetal groups and mixtures thereof. $R^{312}$, $R^{313}$ and $R^{314}$ are each independently a hydrogen atom, a straight, branched or cyclic $C_1$-$C_{10}$ alkyl group, aryl group or aralkyl group.

Also included are amine compounds having a benzimidazole structure and a polar functional group, represented by the general formula (Am-8).

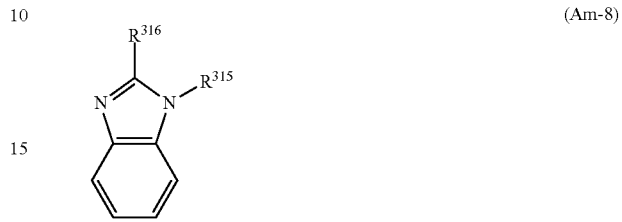
(Am-8)

Herein, $R^{315}$ is a straight, branched or cyclic $C_1$-$C_{20}$ alkyl group in which some or all hydrogen atoms may be substituted by fluorine atoms and which has one or more polar functional groups. The alkyl group contains as the polar functional group at least one group selected from among ester, acetal and cyano groups, and may additionally contain at least one group selected from among hydroxyl, carbonyl, ether, sulfide and carbonate groups. $R^{316}$ is a hydrogen atom, a straight, branched or cyclic $C_1$-$C_{10}$ alkyl group, aryl group or aralkyl group.

Further included are heterocyclic nitrogen-containing compounds having a polar functional group, represented by the general formulae (Am-9) and (Am-10).

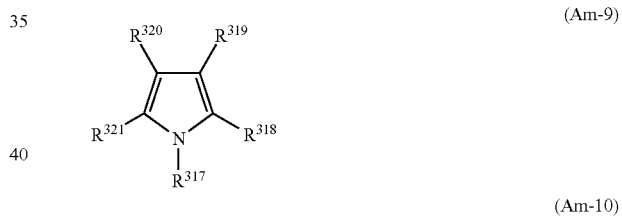
(Am-9)

(Am-10)

Herein, J is a nitrogen atom or =C—$R^{323}$. K is a nitrogen atom or =C—$R^{324}$. $R^{317}$ is a straight, branched or cyclic $C_2$-$C_{20}$ alkyl group in which some or all hydrogen atoms may be substituted by fluorine atoms and which has one or more polar functional groups, the polar functional group being selected from among hydroxyl, carbonyl, ester, ether, sulfide, carbonate, cyano and acetal groups and mixtures thereof. $R^{318}$, $R^{319}$, $R^{320}$ and $R^{321}$ are each independently a hydrogen atom, a straight, branched or cyclic $C_1$-$C_{10}$ alkyl group or aryl group, or a pair of $R^{318}$ and $R^{319}$ and a pair of $R^{320}$ and $R^{321}$, taken together, may form a benzene, naphthalene or pyridine ring. $R^{322}$ is a hydrogen atom, a straight, branched or cyclic $C_1$-$C_{10}$ alkyl group or aryl group. $R^{323}$ and $R^{324}$ each are a hydrogen atom, a straight, branched or cyclic $C_1$-$C_{10}$ alkyl group or aryl group, or a pair of $R^{322}$ and $R^{324}$, taken together, may form a benzene or naphthalene ring.

Also included are amine compounds having an aromatic carboxylic acid ester structure, represented by the general formulae (Am-11) to (Am-14).

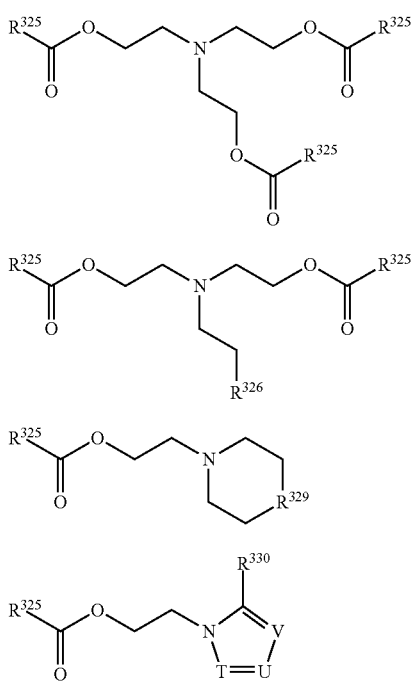

(Am-11)

(Am-12)

(Am-13)

(Am-14)

Herein $R^{325}$ is a $C_6$-$C_{20}$ aryl group or $C_4$-$C_{20}$ hetero-aromatic group, in which some or all hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{326}$ is $CO_2R^{327}$, $OR^{328}$ or cyano group. $R^{327}$ is a $C_1$-$C_{10}$ alkyl group, in which some methylene groups may be replaced by oxygen atoms. $R^{328}$ is a $C_1$-$C_{10}$ alkyl or acyl group, in which some methylene groups may be replaced by oxygen atoms. $R^{329}$ is a single bond, methylene, ethylene, sulfur atom or —O(CH$_2$CH$_2$O)$_h$— group wherein h is 0, 1, 2, 3 or 4. $R^{330}$ is hydrogen, methyl, ethyl or phenyl. T is a nitrogen atom or $CR^{331}$. U is a nitrogen atom or $CR^{332}$. V is a nitrogen atom or $CR^{333}$. $R^{331}$, $R^{332}$ and $R^{333}$ are each independently hydrogen, methyl or phenyl. Alternatively, a pair of $R^{331}$ and $R^{332}$ or a pair of $R^{332}$ and $R^{333}$ may bond together to form a $C_6$-$C_{20}$ aromatic ring or $C_2$-$C_{20}$ hetero-aromatic ring.

Further included are amine compounds of 7-oxanorbornane-2-carboxylic ester structure, represented by the general formula (Am-15).

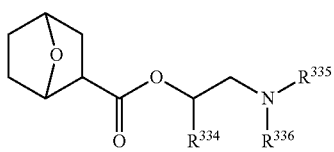

(Am-15)

Herein $R^{334}$ is hydrogen or a straight, branched or cyclic $C_1$-$C_{10}$ alkyl group. $R^{335}$ and $R^{336}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{335}$ and $R^{336}$, taken together, may form a heterocyclic or hetero-aromatic ring of 2 to 20 carbon atoms.

The quenchers may be used alone or in admixture of two or more. The quencher is preferably formulated in an amount of 0.001 to 2 parts, and especially 0.01 to 1 part by weight, per 100 parts by weight of the base resin. Less than 0.001 phr of the quencher may achieve no addition effect whereas more than 2 phr may lead to too low a sensitivity.

Component E

In one preferred embodiment, the resist composition further contains (E) a compound capable of generating an acid upon exposure to high-energy radiation (e.g., UV, deep UV, electron beam, x-ray, excimer laser beam, gamma-ray or synchrotron radiation), that is, an auxiliary photoacid generator other than the photoacid generator of formula (1a). Suitable auxiliary photoacid generators include sulfonium salts, iodonium salts, sulfonyldiazomethane, N-sulfonyloxydicarboxyimide, O-arylsulfonyloxime and O-alkylsulfonyloxime photoacid generators. Exemplary auxiliary photoacid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenyldiphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl) difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide.

A typical tris(substituted alkylsulfonyl)methide is tris(trifluoromethylsulfonyl)methide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl) difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkylsulfonyl)methide is tris(trifluoromethylsulfonyl)methide. Iodonium salts based on combination of the foregoing examples are included.

Exemplary sulfonyldiazomethane compounds include bis-sulfonyldiazomethane compounds and sulfonyl-carbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(4-acetyloxyphenylsulfonyl)diazomethane, bis(4-(methanesulfonyloxy)phenylsulfonyl)diazomethane, bis(4-(p-toluenesulfonyloxy)phenylsulfonyl)diazomethane, bis(4-n-hexyloxyphenylsulfonyl)diazomethane, bis(2-methyl-4-n-hexyloxyphenylsulfonyl)diazomethane, bis(2,5-dimethyl-4-n-hexyloxyphenylsulfonyl)diazomethane, bis(3,5-dimethyl-4-n-hexyloxyphenylsulfonyl)diazomethane, bis(2-methyl-5-isopropyl-4-n-hexyloxyphenylsulfonyl)diazomethane, bis(2-naphthylsulfonyl)diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxydicarboxyimide photoacid generators include combinations of imide skeletons with sulfonates. Exemplary imide skeletons are succinimide, naphthalenedicarboxyimide, phthalimide, cyclohexyldicarboxyimide, 5-norbornene-2,3-dicarboxyimide, and 7-oxabicyclo[2.2.1]-5-heptene-2,3-dicarboxyimide. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy) naphthalene-2-sulfonate, 4-(p-toluenesulfonyloxy) naphthalene-1-sulfonate, 5-(p-toluenesulfonyloxy) naphthalene-1-sulfonate, 8-(p-toluenesulfonyloxy) naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Benzoinsulfonate photoacid generators include benzoin tosylate, benzoin mesylate, and benzoin butanesulfonate.

Pyrogallol trisulfonate photoacid generators include pyrogallol, phloroglucin, catechol, resorcinol, hydroquinone, in which all the hydroxyl groups are substituted by trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, 4-oxo-1-adamantyloxycarbonyldifluoromethanesulfonate, etc.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, 4-oxo-1-adamantyloxycarbonyldifluoromethanesulfonate, etc. Also useful are nitrobenzyl sulfonate analogues in which the nitro group on the benzyl side is substituted by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Suitable O-arylsulfonyloxime compounds and O-alkylsulfonyloxime compounds (oxime sulfonates) include photoacid generators in the form of glyoxime derivatives; photoacid generators in the form of oxime sulfonates with a long conjugated system separated by thiophene or cyclohexadiene; oxime sulfonates having an electron withdrawing group such as trifluoromethyl incorporated for increased stability; oxime sulfonates using phenylacetonitrile or substituted acetonitrile derivatives; and bisoxime sulfonates.

Photoacid generators in the form of glyoxime derivatives include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedionedioxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-

(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(4-fluorobenzenesulfonyl)-α-dimethylglyoxime, bis-O-(4-trifluoromethylbenzenesulfonyl)-α-dimethylglyoxime, bis-O-(xylenesulfonyl)-α-dimethylglyoxime, bis-O-(trifluoromethanesulfonyl)-nioxime, bis-O-(2,2,2-trifluoroethanesulfonyl)-nioxime, bis-O-(10-camphorsulfonyl)-nioxime, bis-O-(benzenesulfonyl)-nioxime, bis-O-(4-fluorobenzenesulfonyl)-nioxime, bis-O-(4-(trifluoromethyl)benzenesulfonyl)-nioxime, and bis-O-(xylenesulfonyl)-nioxime. Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Photoacid generators in the form of oxime sulfonates with a long conjugated system separated by thiophene or cyclohexadiene include (5-(p-toluenesulfonyl)oxyimino-5H-thiophen-2-ylidene)phenylacetonitrile, (5-(10-camphorsulfonyl)oxyimino-5H-thiophen-2-ylidene)phenylacetonitrile, (5-n-octanesulfonyloxyimino-5H-thiophen-2-ylidene)phenylacetonitrile, (5-(p-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methylphenyl)acetonitrile, (5-(4-(p-toluenesulfonyloxy)benzenesulfonyl)oxyimino-5H-thiophen-2-ylidene)phenylacetonitrile, and (5-(2,5-bis(p-toluenesulfonyloxy)benzenesulfonyl)oxyimino-5H-thiophen-2-ylidene)phenylacetonitrile. Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Suitable oxime sulfonates having an electron withdrawing group such as trifluoromethyl incorporated for increased stability include 2,2,2-trifluoro-1-phenyl-ethanone O-(methylsulfonyl)oxime, 2,2,2-trifluoro-1-phenyl-ethanone O-(10-camphorsulfonyl)oxime, 2,2,2-trifluoro-1-phenylethanone O-(4-methoxybenzenesulfonyl)oxime, 2,2,2-trifluoro-1-phenylethanone O-(1-naphthylsulfonyl)oxime, 2,2,2-trifluoro-1-phenylethanone O-(2-naphthylsulfonyl)oxime, 2,2,2-trifluoro-1-phenylethanone O-(2,4,6-trimethylphenylsulfonyl)oxime, 2,2,2-trifluoro-1-(4-methylphenyl)ethanone O-(10-camphorsulfonyl)oxime, 2,2,2-trifluoro-1-(4-methylphenyl)ethanone O-(methylsulfonyl)oxime, 2,2,2-trifluoro-1-(2-methylphenyl)ethanone O-(10-camphorsulfonyl)oxime, 2,2,2-trifluoro-1-(2,4-dimethylphenyl)ethanone O-(10-camphorsulfonyl)oxime, 2,2,2-trifluoro-1-(2,4-dimethylphenyl)ethanone O-(1-naphthylsulfonyl)oxime, 2,2,2-trifluoro-1-(2,4-dimethylphenyl)-ethanone O-(2-naphthylsulfonyl)oxime, 2,2,2-trifluoro-1-(2,4,6-trimethylphenyl)ethanone O-(10-camphorsulfonyl)oxime, 2,2,2-trifluoro-1-(2,4,6-trimethylphenyl)ethanone O-(1-naphthylsulfonyl)oxime, 2,2,2-trifluoro-1-(2,4,6-trimethylphenyl)ethanone O-(2-naphthylsulfonyl)oxime, 2,2,2-trifluoro-1-(4-methoxyphenyl)ethanone O-(methylsulfonyl)oxime, 2,2,2-trifluoro-1-(4-methylthiophenyl)-ethanone O-(methylsulfonyl)oxime, 2,2,2-trifluoro-1-(3,4-dimethoxyphenyl)ethanone O-(methylsulfonyl)oxime, 2,2,2-trifluoro-1-(4-methoxyphenyl)ethanone O-(4-methylphenylsulfonyl)oxime, 2,2,2-trifluoro-1-(4-methoxyphenyl)ethanone O-(4-methoxyphenylsulfonyl)oxime, 2,2,2-trifluoro-1-(4-methoxyphenyl)ethanone O-(4-dodecylphenylsulfonyl)oxime, 2,2,2-trifluoro-1-(4-methoxyphenyl)ethanone O-(octylsulfonyl)oxime, 2,2,2-trifluoro-1-(4-thiomethylphenyl)ethanone O-(4-methoxyphenylsulfonyl)oxime, 2,2,2-trifluoro-1-(4-thiomethylphenyl)ethanone O-(4-dodecylphenylsulfonyl)oxime, 2,2,2-trifluoro-1-(4-thiomethylphenyl)ethanone O-(octylsulfonyl)oxime, 2,2,2-trifluoro-1-(4-thiomethylphenyl)ethanone O-(2-naphthylsulfonyl)oxime, 2,2,2-trifluoro-1-(2-methylphenyl)ethanone O-(methylsulfonyl)oxime, 2,2,2-trifluoro-1-(4-methylphenyl)ethanone O-(phenylsulfonyl)oxime, 2,2,2-trifluoro-1-(4-chlorophenyl)ethanone O-(phenylsulfonyl)oxime, 2,2,3,3,4,4,4-heptafluoro-1-phenylbutanone O-(10-camphorsulfonyl)oxime, 2,2,2-trifluoro-1-(1-naphthyl)ethanone O-(methylsulfonyl)oxime, 2,2,2-trifluoro-1-(2-naphthyl)ethanone O-(methylsulfonyl)oxime, 2,2,2-trifluoro-1-(4-benzylphenyl)ethanone O-(methylsulfonyl)oxime, 2,2,2-trifluoro-1-(4-(phenyl-1,4-dioxa-but-1-yl)phenyl) ethanone O-(methylsulfonyl)oxime, 2,2,2-trifluoro-1-(1-naphthyl)ethanone O-(propylsulfonyl)oxime, 2,2,2-trifluoro-1-(2-naphthyl)ethanone O-(propylsulfonyl)oxime, 2,2,2-trifluoro-1-(4-benzylphenyl)ethanone O-(propylsulfonyl)oxime, 2,2,2-trifluoro-1-(4-methylsulfonylphenyl)ethanone O-(propylsulfonyl)oxime, 2,2,2-trifluoro-1-(4-methylsulfonyloxyphenyl)ethanone O-(propylsulfonyl)oxime, 2,2,2-trifluoro-1-(4-methylcarbonyloxyphenyl)ethanone O-(propylsulfonyl)oxime, 2,2,2-trifluoro-1-(6H,7H-5,8-dioxonaphth-2-yl)ethanone O-(propylsulfonyl)oxime, 2,2,2-trifluoro-1-(4-methoxycarbonylmethoxyphenyl)ethanone O-(propylsulfonyl)oxime, 2,2,2-trifluoro-1-(4-methoxycarbonyl)-(4-amino-1-oxa-pent-1-yl)phenyl)ethanone O-(propylsulfonyl)oxime, 2,2,2-trifluoro-1-(3,5-dimethyl-4-ethoxyphenyl)ethanone O-(propylsulfonyl)oxime, 2,2,2-trifluoro-1-(4-benzyloxyphenyl)ethanone O-(propylsulfonyl)oxime, 2,2,2-trifluoro-1-(2-thiophenyl)ethanone O-(propylsulfonate)oxime, and 2,2,2-trifluoro-1-(1-dioxathiophen-2-yl) ethanone O-(propylsulfonate)oxime; 2,2,2-trifluoro-1-(4-(3-(4-(2,2,2-trifluoro-1-(trifluoro-methanesulfonyloxyimino) ethyl)phenoxy)propoxy)phenyl)ethanone O-(trifluoromethanesulfonyl)oxime, 2,2,2-trifluoro-1-(4-(3-(4-(2,2,2-trifluoro-1-(1-propane-sulfonyloxyimino)ethyl) phenoxy)propoxy)phenyl)ethanone O-(propylsulfonyl)oxime, 2,2,2-trifluoro-1-(4-(3-(4-(2,2,2-trifluoro-1-(1-butane-sulfonyloxyimino)ethyl)phenoxy)propoxy)phenyl) ethanone O-(butylsulfonyl)oxime, 2,2,2-trifluoro-1-(4-(3-(4-(2,2,2-trifluoro-1-(4-(4-methyl-phenylsulfonyloxy) phenylsulfonyloxyimino)ethyl)phenoxy)propoxy)phenyl) ethanone O-(4-(4-methylphenylsulfonyloxy) phenylsulfonyl)oxime, and 2,2,2-trifluoro-1-(4-(3-(4-(2,2,2-trifluoro-1-(2,5-bis(4-methylphenylsulfonyloxy) benzenesulfonyloxy)phenylsulfonyloxyimino)ethyl) phenoxy)propoxy)phenyl)ethanone O-(2,5-bis(4-methylphenylsulfonyloxy)benzenesulfonyloxy) phenylsulfonyl)oxime.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl) difluoromethanesulfonate, and 4-oxo-1-adamantyloxycarbonyldifluoromethanesulfonate.

Also included are oxime sulfonates having the formula (Ox-1):

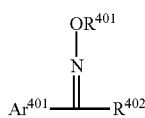

(Ox-1)

wherein $R^{401}$ is a substituted or unsubstituted $C_1$-$C_{10}$ haloalkylsulfonyl or halobenzenesulfonyl group, $R^{402}$ is a $C_1$-$C_{11}$ haloalkyl group, and $Ar^{401}$ is substituted or unsubstituted aromatic or hetero-aromatic group.

Examples include 2-[2,2,3,3,4,4,5,5-octafluoro-1-(nonafluorobutylsulfonyloxyimino)-pentyl]fluorene, 2-[2,2,3,3,4,4-pentafluoro-1-(nonafluorobutylsulfonyloxyimino)-butyl]fluorene, 2-[2,2,3,3,4,4,5,5,6,6-decafluoro-1-(nonafluorobutylsulfonyloxyimino)-hexyl]fluorene, 2-[2,2,3,3,4,4,5,5-octafluoro-1-(nonafluorobutylsulfonyloxyimino)-pentyl]-4-biphenyl, 2-[2,2,3,3,4,4-pentafluoro-1-(nonafluorobutylsulfonyloxyimino)-butyl]-4-biphenyl, and 2-[2,2,3,3,4,4,5,5,6,6-decafluoro-1-(nonafluorobutylsulfonyloxyimino)-hexyl]-4-biphenyl.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl) difluoromethanesulfonate, and 4-oxo-1-adamantyloxycarbonyldifluoromethanesulfonate.

Suitable oxime sulfonate generators using substituted acetonitrile derivatives include α-(p-toluenesulfonyloxyimino)-phenylacetonitrile, α-(p-chlorobenzenesulfonyloxyimino)-phenylacetonitrile, α-(4-nitrobenzenesulfonyloxyimino)-phenylacetonitrile, α-(4-nitro-2-trifluoromethylbenzenesulfonyloxyimino)-phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenylacetonitrile, α-(benzenesulfonyloxyimino)-2-thienylacetonitrile, α-(4-dodecylbenzenesulfonyloxyimino)-phenylacetonitrile, α-[(4-toluenesulfonyloxyimino)-4-methoxyphenyl]acetonitrile, α-[(dodecylbenzenesulfonyloxyimino)-4-methoxyphenyl] acetonitrile, α-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile. Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2- tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Suitable bisoxime sulfonates include bis(α-(p-toluenesulfonyloxy)imino)-p-phenylenediacetonitrile, bis(α-(benzenesulfonyloxy)imino)-p-phenylenediacetonitrile, bis(α-(methanesulfonyloxy)imino)-p-phenylenediacetonitrile, bis(α-(butanesulfonyloxy)imino)-p-phenylenediacetonitrile, bis(α-(10-camphorsulfonyloxy)imino)-p-phenylenediacetonitrile, bis(α-(trifluoromethanesulfonyloxy)imino)-p-phenylenediacetonitrile, bis(α-(4-methoxybenzenesulfonyloxy)imino)-p-phenylenediacetonitrile, bis(α-(4-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediacetonitrile, bis(α-(10-camphorsulfonyloxy)imino)-m-phenylenediacetonitrile, bis(α-(trifluoromethanesulfonyloxy)imino)-m-phenylenediacetonitrile, bis(α-(4-methoxybenzenesulfonyloxy)imino)-m-phenylenediacetonitrile, etc.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

When the photoacid generator (E) is added to the KrF excimer laser resist composition, preference is given to sulfonium salts, bissulfonyldiazomethanes, N-sulfonyloxyimides and oxime-O-sulfonates.

Illustrative preferred photoacid generators include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(p-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(p-toluenesulfonyloxy)benzenesulfonate, 4-tert-butylphenyldiphenylsulfonium camphorsulfonate, tris(4-methylphenyl)sulfonium camphorsulfonate, tris(4-tert-butylphenyl)sulfonium camphorsulfonate, bis(tert-butylsulfonyl)diazomethane, bis(cyclohexylsulfonyl)diazomethane, bis(2,4-dimethylphenylsulfonyl)diazomethane, bis(4-n-hexyloxyphenylsulfonyl)diazomethane, bis(2-methyl-4-n-hexyloxyphenylsulfonyl)diazomethane, bis(2,5-dimethyl-4-n-hexyloxyphenylsulfonyl)diazomethane, bis(3,5-dimethyl-4-n-hexyloxyphenylsulfonyl)diazomethane, bis(2-methyl-5-isopropyl-4-n-hexyloxy)phenylsulfonyldiazomethane, bis(4-tert-butylphenylsulfonyl)diazomethane, N-camphorsulfonyloxy-5-norbornene-2,3-dicarboxylic acid imide, N-p-toluenesulfonyloxy-5-norbornene-2,3-dicarboxylic acid imide, (5-(10-camphorsulfonyl)oxyimino-5H-thiophen-2-ylidene)(2-methylphenyl)acetonitrile, and (5-(p-toluenesulfonyl)oxyimino-5H-thiophen-2-ylidene)(2-methylphenyl)acetonitrile.

When the photoacid generator (E) is added to the ArF laser resist composition, preference is given to sulfonium salts and oxime-O-sulfonates. Illustrative preferred photoacid generators include triphenylsulfonium trifluoromethanesulfonate, triphenylsulfonium pentafluoroethanesulfonate, triphenylsulfonium heptafluoropropanesulfonate, triphenylsulfonium nonafluorobutanesulfonate, triphenylsulfonium tridecafluorohexanesulfonate, triphenylsulfonium heptadecafluorooctanesulfonate, triphenylsulfonium perfluoro(4-ethylcyclohexane)sulfonate, 4-methylphenyldiphenylsulfonium nonafluorobutanesulfonate, 2-oxo-2-phenylethylthiacyclopentanium nonafluorobutanesulfonate, 4-tert-butylphenyldiphenylsulfonium nonafluorobutanesulfonate, 4-tert-butylphenyldiphenylsulfonium perfluoro(4-ethylcyclohexane)sulfonate, 4-tert-butylphenyldiphenylsulfonium heptafluorooctanesulfonate, triphenylsulfonium 1,1-difluoro-2-naphthylethanesulfonate, triphenylsulfonium 1,1,2,2-tetrafluoro-2-(norbornan-2-yl)ethanesulfonate, triphenylsulfonium 2-benzoyloxy-1,1,3,3,3-pentafluoropropanesulfonate, triphenylsulfonium 1,1,3,3,3-pentafluoro-2-(pivaloyloxy)propanesulfonate, triphenylsulfonium 2-(cyclohexanecarbonyloxy)-1,1,3,3,3-pentafluoropropanesulfonate, triphenylsulfonium 2-(2-naphthoyloxy)-1,1,3,3,3-pentafluoropropanesulfonate, triphenylsulfonium 2-(1-adamantanecarbonyloxy)-1,1,3,3,3-pentafluoropropanesulfonate, triphenylsulfonium 2-hydroxy-1,1,3,3,3-pentafluoropropanesulfonate, triphenylsulfonium adamantanemethoxycarbonyldifluoromethanesulfonate, triphenylsulfonium 1-(3-hydroxymethyladamantane)methoxycarbonyldifluoromethanesulfonate, triphenylsulfonium methoxycarbonyldifluoromethanesulfonate, 4-tert-butylphenyldiphenylsulfonium 2-benzoyloxy-1,1,3,3,3-pentafluoropropanesulfonate, 4-tert-butylphenyldiphenylsulfonium 1,1,3,3,3-pentafluoro-2-(pivaloyloxy)propanesulfonate, 4-tert-butylphenyldiphenylsulfonium 2-(cyclohexanecarbonyloxy)-1,1,3,3,3-pentafluoropropanesulfonate, 4-tert-butylphenyldiphenylsulfonium 2-(2-naphthoyloxy)-1,1,3,3,3-pentafluoropropanesulfonate, 4-tert-butylphenyldiphenylsulfonium 2-(1-adamantanecarbonyloxy)-1,1,3,3,3-pentafluoropropanesulfonate, 4-tert-butylphenyldiphenylsulfonium 2-hydroxy-1,1,3,3,3-pentafluoropropanesulfonate, 4-tert-butylphenyldiphenylsulfonium adamantanemethoxycarbonyldifluoromethanesulfonate, 4-tert-butylphenyldiphenylsulfonium 1-(3-hydroxymethyladamantane)methoxycarbonyldifluoromethanesulfonate, 4-tert-butylphenyldiphenylsulfonium methoxycarbonyldifluoromethanesulfonate, 2-oxo-2-phenylethylthiacyclopentanium 2-benzoyloxy-1,1,3,3,3-pentafluoropropanesulfonate, 2-oxo-2-phenylethylthiacyclopentanium 2-cyclohexanecarbonyloxy-1,1,3,3,3-pentafluoropropanesulfonate, triphenylsulfonium perfluoro(1,3-propylenebissulfonyl)imide, triphenylsulfonium bis(pentafluoroethylsulfonyl)imide, 2-(2,2,3,3,4,4,5,5-octafluoro-1-(nonafluorobutylsulfonyloxyimino)pentyl)fluorene, 2-(2,2,3,3,4,4-pentafluoro-1-(nonafluorobutylsulfonyloxyimino)butyl)fluorene, 2-(2,2,3,3,4,4,5,5,6,6-decafluoro-1-(nonafluorobutylsulfonyloxyimino)hexyl)fluorene, 2-(2,2,3,3,4,4,5,5-octafluoro-1-(2-(cyclohexanecarbonyloxy)-1,1,3,3,3-pentafluoropropanesulfonyloxyimino)pentyl)fluorene, 2-(2,2,3,3,4,4-pentafluoro-1-(2-(cyclohexanecaronyloxy)-1,1,3,3,3-pentafluoropropanesulfonyloxyimino)butyl)fluorene, and 2-(2,2,3,3,4,4,5,5,6,6-decafluoro-1-(nonafluorobutylsulfonyloxyimino)hexyl)fluorene.

When the photoacid generator (E) is added to the ArF immersion lithography resist composition, preference is given to sulfonium salts and oxime-O-sulfonates. Illustrative preferred photoacid generators include triphenylsulfonium nonafluorobutanesulfonate, triphenylsulfonium tridecafluorohexanesulfonate, triphenylsulfonium heptadecafluorooctanesulfonate, triphenylsulfonium perfluoro(4-ethylcyclohexane)sulfonate, 4-methylphenyldiphenylsulfonium nonafluorobutanesulfonate, 2-oxo-2-phenylethylthiacyclopentanium nonafluorobutanesulfonate, 4-tert-butylphenyldiphenylsulfonium nonafluorobutanesulfonate, 4-tert-butylphenyldiphenylsulfonium perfluoro(4-ethylcyclohexane)sulfonate, 4-tert-butylphenyldiphenylsulfonium heptafluorooctanesulfonate, triphenylsulfonium 1,1-difluoro-2-naphthylethanesulfonate, triphenylsulfonium 1,1,2,2-tetrafluoro-2-(norbornan-2-yl)ethanesulfonate, triphenylsulfonium 2-benzoyloxy-1,1,3,3,3-pentafluoropropanesulfonate, triphenylsulfonium 1,1,3,3,3-pentafluoro-2-(pivaloyloxy)propanesulfonate, triphenylsulfonium 2-(cyclohexanecarbonyloxy)-1,1,3,3,3-pentafluoropropanesulfonate, triphenylsulfonium 2-(2-naphthoyloxy)-1,1,3,3,3-pentafluoropropanesulfonate, triphenylsulfonium 2-(1-adamantanecarbonyloxy)-1,1,3,3,3-pentafluoropropanesulfonate, triphenylsulfonium 2-hydroxy-1,1,3,3,3-pentafluoropropanesulfonate, triphenylsulfonium adamantanemethoxycarbonyldifluoromethanesulfonate, triphenylsulfonium 1-(3-hydroxymethyladamantane)methoxycarbonyldifluoromethanesulfonate, triphenylsulfonium methoxycarbonyldifluoromethanesulfonate, 4-tert-butylphenyldiphenylsulfonium 2-benzoyloxy-1,1,3,3,3-pentafluoropropanesulfonate, 4-tert-butylphenyldiphenylsulfonium 1,1,3,3,3-pentafluoro-2-(pivaloyloxy)propanesulfonate, 4-tert-butylphenyldiphenylsulfonium 2-(cyclohexanecarbonyloxy)-1,1,3,3,3-pentafluoropropanesulfonate, 4-tert-butylphenyldiphenylsulfonium 2-(2-naphthoyloxy)-1,1,3,3,3-pentafluoropropanesulfonate, 4-tert-butylphenyldiphenylsulfonium 2-(1-adamantanecarbonyloxy)-1,1,3,3,3-pentafluoropropanesulfonate, 4-tert-butylphenyldiphenylsulfonium 2-hydroxy-1,1,3,3,3-pentafluoropropanesulfonate, 4-tert-butylphenyldiphenylsulfonium adamantanemethoxycarbonyldifluoromethanesulfonate, 4-tert-butylphenyldiphenylsulfonium 1-(3-hydroxymethyladamantane)methoxycarbonyldifluoromethanesulfonate, 4-tert-butylphenyldiphenylsulfonium methoxycarbonyldifluoromethanesulfonate, 2-oxo-2-phenylethylthiacyclopentanium 2-benzoyloxy-1,1,3,3,3-pentafluoropropanesulfonate, 2-oxo-2-phenylethylthiacyclopentanium 2-cyclohexanecarbonyloxy-1,1,3,3,3-pentafluoropropanesulfonate, triphenylsulfonium perfluoro(1,3-propylenebissulfonyl)imide, triphenylsulfonium bis(pentafluoroethylsulfonyl)imide, 2-(2,2,3,3,4,4,5,5-octafluoro-1-(nonafluorobutylsulfonyloxyimino)pentyl)fluorene, 2-(2,2,3,3,4,4-pentafluoro-1-(nonafluorobutylsulfonyloxyimino)butyl)fluorene, 2-(2,2,3,3,4,4,5,5,6,6-decafluoro-1-(nonafluorobutylsulfonyloxyimino)hexyl)fluorene, 2-(2,2,3,3,4,4,5,5-octafluoro-1-(2-(cyclohexanecarbonyloxy)-1,1,3,3,3-pentafluoropropanesulfonyloxyimino)pentyl)fluorene, 2-(2,2,3,3,4,4-pentafluoro-1-(2-(cyclohexanecarbonyloxy)-1,1,3,3,3-pentafluoropropanesulfonyloxyimino)butyl)fluorene, and 2-(2,2,3,3,4,4,5,5,6,6-decafluoro-1-(nonafluorobutylsulfonyloxyimino)hexyl)fluorene.

In the chemically amplified resist composition, the auxiliary photoacid generator (E) may be added in any desired amount as long as the objects of the invention are not compromised. An appropriate amount of the auxiliary photoacid generator (E) is 0.1 to 10 parts, and more preferably 0.1 to 5 parts by weight per 100 parts by weight of the base resin in the composition. Too high a proportion of the auxiliary photoacid generator (E) may give rise to problems of degraded resolution and foreign matter upon development and resist film peeling. The auxiliary photoacid generators may be used alone or in admixture of two or more. The transmittance of the resist film can be controlled by using an (auxiliary) photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid and an onium salt capable of generating a weak acid are used in admixture, an exchange from the strong acid to the weak acid as above can take place, but it never happens that the weak acid collides with the unreacted onium salt capable of generating a strong acid to induce a salt exchange. This is because of a likelihood of an onium cation forming an ion pair with a stronger acid anion.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Component F

Component (F) is an organic acid derivative and/or a fluorinated alcohol. Illustrative, non-limiting, examples of the organic acid derivatives include phenol, cresol, catechol, resorcinol, pyrogallol, phloroglucin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

The fluorinated alcohol is an alcohol which is substituted with fluorine atoms except α-position. Those compounds terminated with 1,1,1,3,3,3-hexafluoro-2-propanol are desirable although the fluorinated alcohols are not limited thereto. Illustrative examples of the desirable fluorinated alcohols are given below.

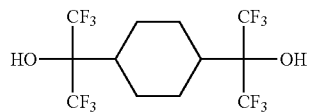

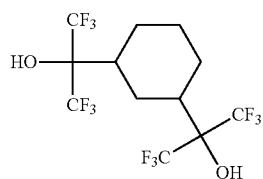

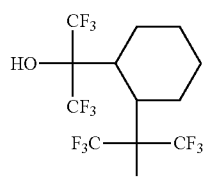

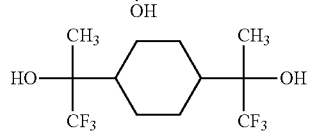

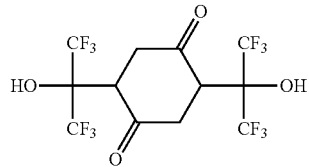

-continued

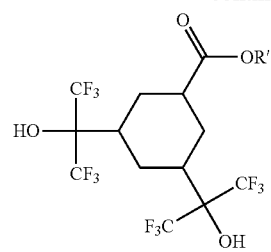

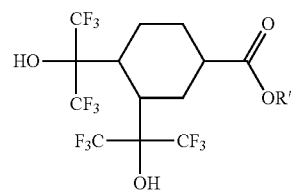

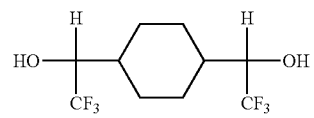

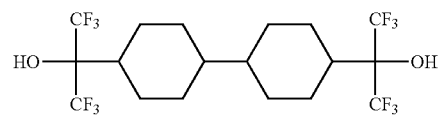

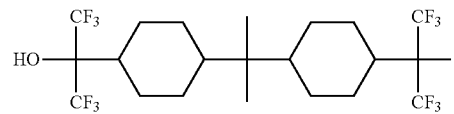

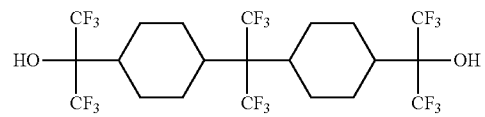

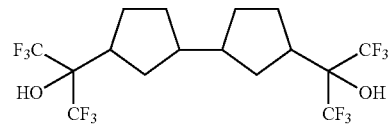

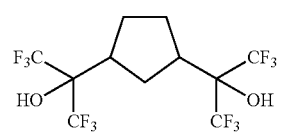

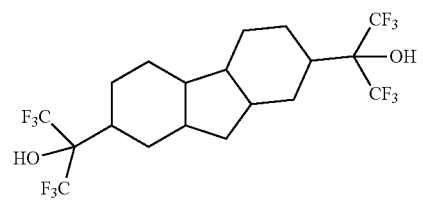

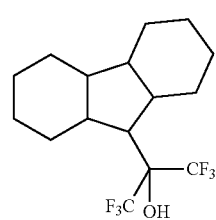

41
-continued
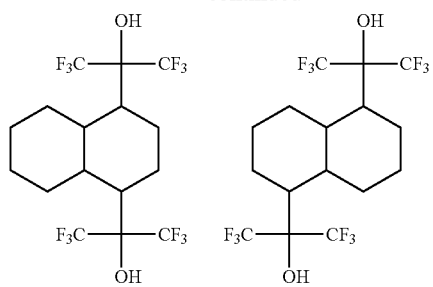
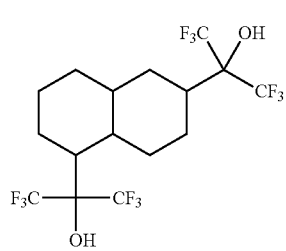
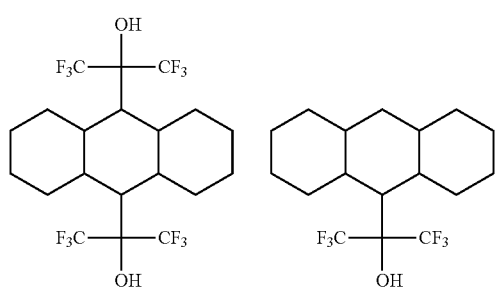
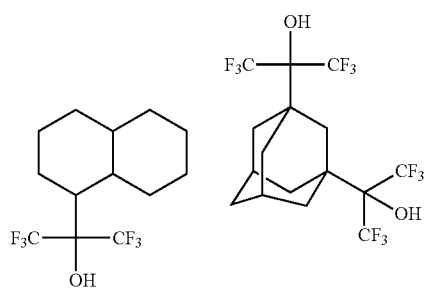
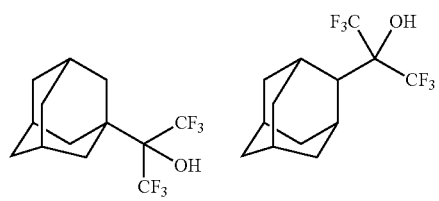
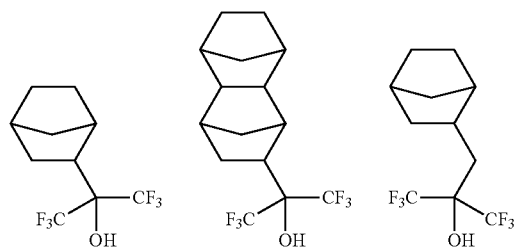
42
-continued
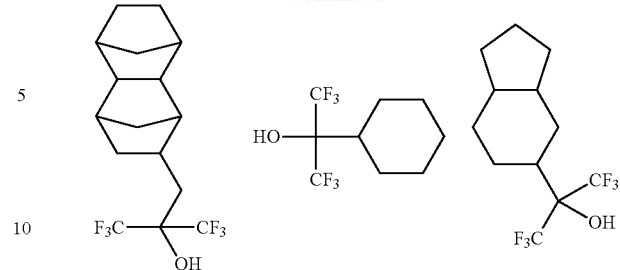
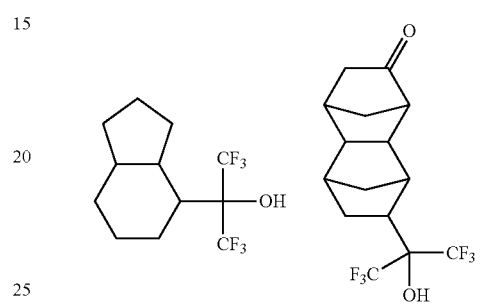
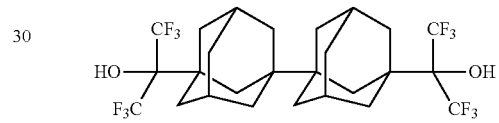
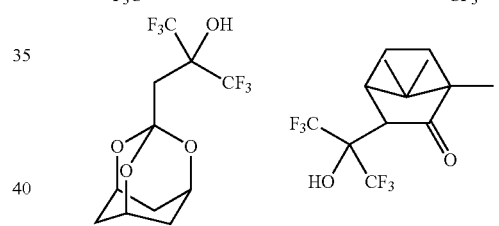
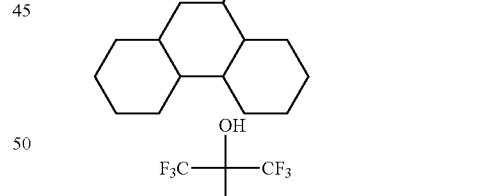
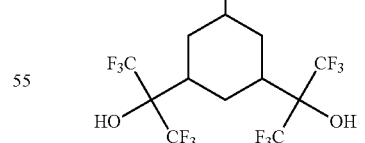
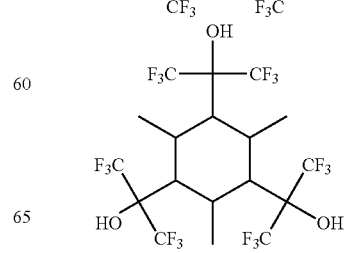

-continued
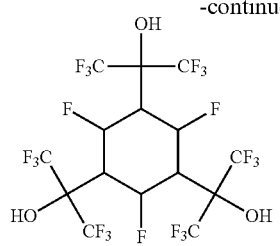
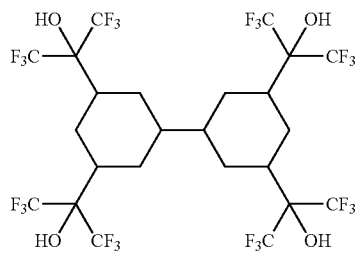
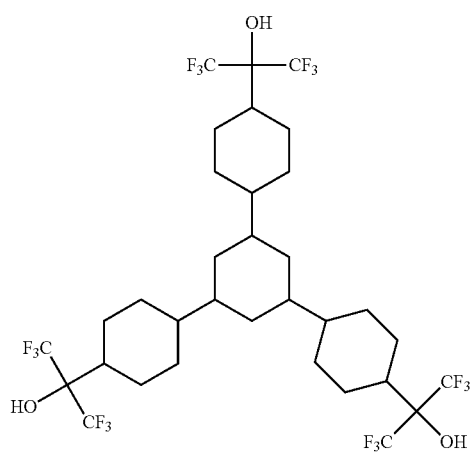
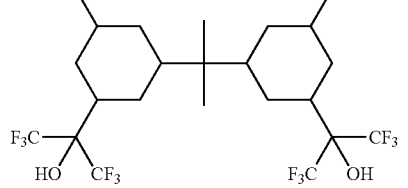
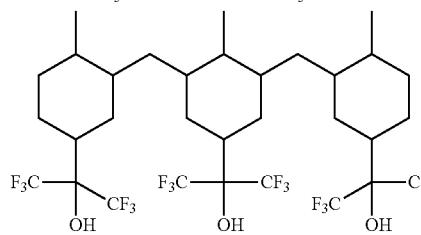
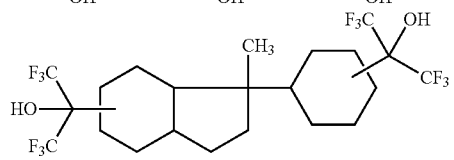
-continued
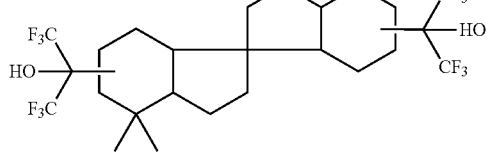
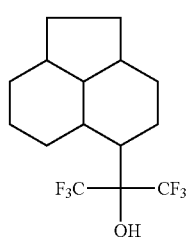
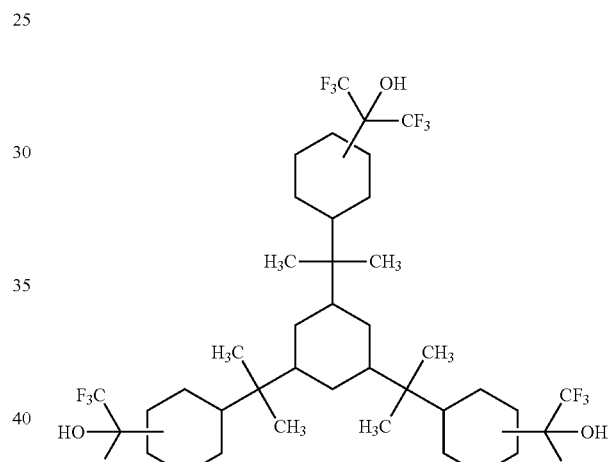
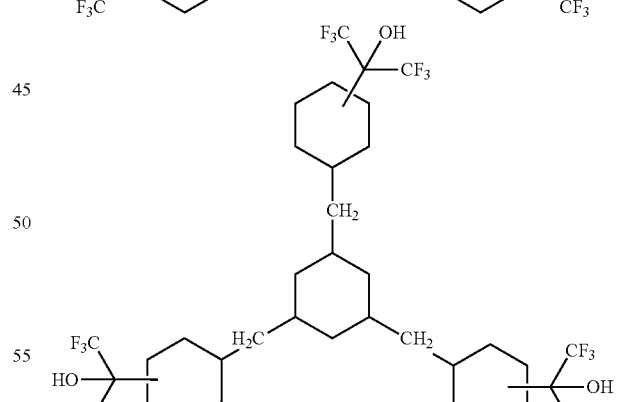
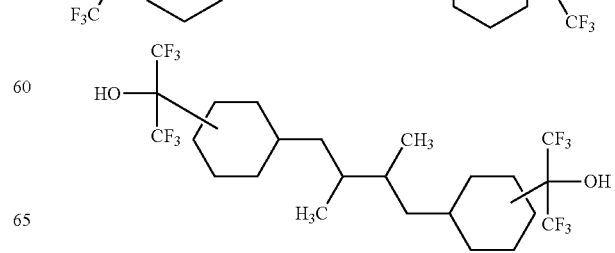

-continued

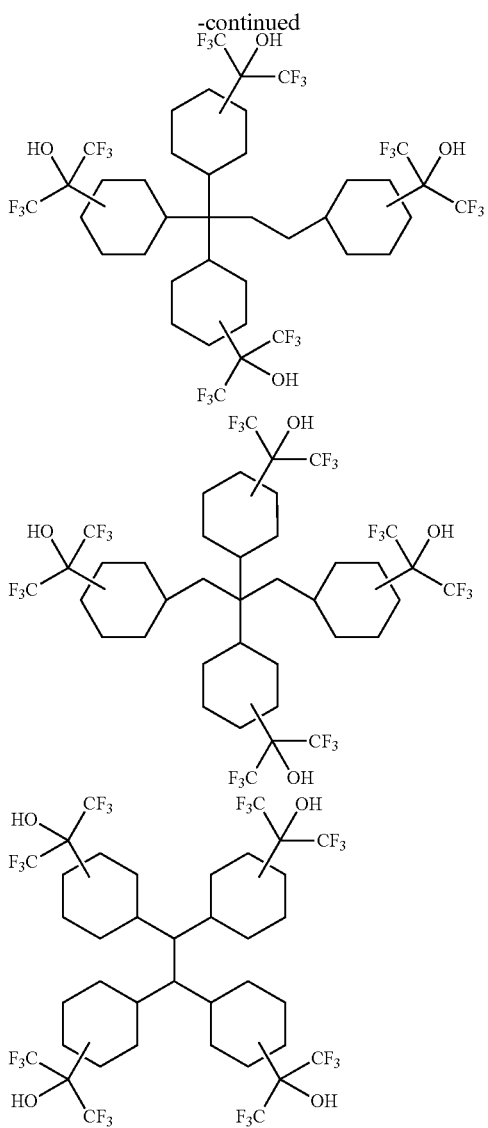

Note that R' is selected from $C_2$-$C_{30}$ acetal groups and $C_4$-$C_{30}$ tertiary alkyl groups having formulae (C1) and (C2) which have been described in the "base resin" section.

In the chemically amplified resist composition of the invention, the organic acid derivative or fluorinated alcohol is preferably formulated in an amount of up to 5 parts, and especially up to 1 part by weight, per 100 parts by weight of the base resin. More than 5 phr may result in too low a resolution. Depending on the combination of the other components in the resist composition, the organic acid derivative and fluorinated alcohol may be omitted.

Component G

In one preferred embodiment, the resist composition further contains (G) a compound with a weight average molecular weight of up to 3,000 which changes its solubility in an alkaline developer under the action of an acid, that is, a dissolution inhibitor. Typically, a compound obtained by substituting acid labile substituents for some or all hydrogen atoms of hydroxyl groups on a phenol or carboxylic acid derivative having a low molecular weight of up to 2,500 or fluorinated alcohol is added as the dissolution inhibitor.

Examples of the phenol or carboxylic acid derivative having a weight average molecular weight of up to 2,500 include bisphenol A, bisphenol H, bisphenol S, 4,4-bis(4'-hydroxyphenyl)valeric acid, tris(4-hydroxyphenyl)methane, 1,1,1-tris(4'-hydroxyphenyl)ethane, 1,1,2-tris(4'-hydroxyphenyl) ethane, phenolphthalein, thymolphthalein, cholic acid, deoxycholic acid, and lithocholic acid. Examples of the fluorinated alcohol are as described above for component (F). The acid labile substituents are the same as those exemplified as the acid labile groups in the polymer.

Illustrative, non-limiting, examples of the dissolution inhibitors which are useful herein include bis(4-(2'-tetrahydropyranyloxy)phenyl)methane, bis(4-(2'-tetrahydrofuranyloxy)phenyl)methane, bis(4-tert-butoxyphenyl)methane, bis (4-tert-butoxycarbonyloxyphenyl)methane, bis(4-tert-butoxycarbonylmethyloxyphenyl)methane, bis(4-(1'-ethoxyethoxy)phenyl)methane, bis(4-(1'-ethoxypropyloxy) phenyl)methane, 2,2-bis(4'-(2''-tetrahydropyranyloxy)) propane, 2,2-bis(4'-(2''-tetrahydrofuranyloxy)phenyl) propane, 2,2-bis(4'-tert-butoxyphenyl)propane, 2,2-bis(4'-tert-butoxycarbonyloxyphenyl)propane, 2,2-bis(4-tert-butoxycarbonylmethyloxyphenyl)propane, 2,2-bis(4'-(1''-ethoxyethoxy)phenyl)propane, 2,2-bis(4'-(1''-ethoxypropyloxy)phenyl)propane, tert-butyl 4,4-bis(4'-(2''-tetrahydropyranyloxy)phenyl)valerate, tert-butyl 4,4-bis(4'-(2''-tetrahydrofuranyloxy)phenyl)valerate, tert-butyl 4,4-bis (4'-tert-butoxyphenyl)valerate, tert-butyl 4,4-bis(4-tert-butoxycarbonyloxyphenyl)valerate, tert-butyl 4,4-bis(4'-tert-butoxycarbonylmethyloxyphenyl)valerate, tert-butyl 4,4-bis (4'-(1''-ethoxyethoxy)phenyl)valerate, tert-butyl 4,4-bis(4'-(1''-ethoxypropyloxy)phenyl)valerate, tris(4-(2'-tetrahydropyranyloxy)phenyl)methane, tris(4-(2'-tetrahydrofuranyloxy)phenyl)methane, tris(4-tert-butoxyphenyl)methane, tris(4-tert-butoxycarbonyloxyphenyl)methane, tris(4-tert-butoxycarbonyloxymethylphenyl)methane, tris(4-(1'-ethoxyethoxy)phenyl)methane, tris(4-(1'-ethoxypropyloxy) phenyl)methane, 1,1,2-tris(4'-(2''-tetrahydropyranyloxy) phenyl)ethane, 1,1,2-tris(4'-(2''-tetrahydrofuranyloxy) phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, 1,1,2-tris(4'-(1'-ethoxypropyloxy)phenyl)ethane, tert-butyl cholate, tert-butyl deoxycholate, and tert-butyl lithocholate. The compounds described in JP-A 2003-107706 are also useful.

In the resist composition of the invention, an appropriate amount of the dissolution inhibitor (G) is up to 20 parts, and especially up to 15 parts by weight per 100 parts by weight of the base resin. With more than 20 phr of the dissolution inhibitor, the resist composition becomes less heat resistant because of an increased content of monomer components.

Component C'

The base resin used in the negative working resist composition is (C') a base resin which is normally alkali soluble, but becomes substantially alkali insoluble under the action of a crosslinker. It is preferably a precursor resin which will be substituted with acid labile groups to form the base resin (C).

Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

To impart a certain function, suitable substituent groups may be introduced into some of the phenolic hydroxyl and carboxyl groups on the foregoing polymer (to be protected with acid labile groups). Exemplary and preferred are substituent groups for improving adhesion to the substrate, substituent groups for improving etching resistance, and especially substituent groups which are relatively stable against acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isoboronyl, and cyclohexyl. It is also possible to introduce acid-decomposable substituent groups such as tert-butoxycarbonyl and relatively acid-undecomposable substituent groups such as tert-butyl and tert-butoxycarbonylmethyl.

In the resist composition, the resin (C') is blended in any desired amount, preferably of 65 to 99 parts by weight, especially 65 to 98 parts by weight among 100 parts by weight of the total solids.

Component H

Formulated in the negative resist composition is an acid crosslinker (F) which forms a crosslinked structure under the action of acid. Typical crosslinkers are compounds having at least two hydroxymethyl, alkoxymethyl, epoxy or vinyl ether groups within a molecule. Substituted glycoluril derivatives, urea derivatives, and hexa(methoxymethyl)melamine compounds are suitable as the acid crosslinker. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred crosslinkers are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine.

In the chemically amplified resist composition, an appropriate amount of the acid crosslinker is, though not limited thereto, 1 to 20 parts, and especially 5 to 15 parts by weight per 100 parts by weight of the base resin. The crosslinkers may be used alone or in admixture of two or more.

In the chemically amplified resist composition of the invention, there may be added such additives as a surfactant for improving coating characteristics, and a light absorbing agent for reducing diffuse reflection from the substrate.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (JEMCO Inc.), Megaface F171, F172, F173, R08 and R30 (Dai-Nippon Ink & Chemicals, Inc.), Fluorad FC430, FC431, FC-4430 and FC-4432 (Sumitomo 3M Co., Ltd.), Asahiguard AG710, Surflon S-381, S-382, SC101, SC102, SC103, SC104, SC105, SC106, Surfynol E1004, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Inter alia, FC430, Surflon S-381, Surfynol E1004, KH-20 and KH-30 are preferred. These surfactants may be used alone or in admixture.

In the chemically amplified resist composition of the invention, the surfactant is preferably formulated in an amount of up to 2 parts, and especially up to 1 part by weight, per 100 parts by weight of the base resin.

In the chemically amplified resist composition of the invention, a UV absorber may be added. Those UV absorbers described in JP-A 11-190904 are useful, but the invention is not limited thereto. Exemplary UV absorbers are diaryl sulfoxide derivatives such as bis(4-hydroxyphenyl)sulfoxide, bis(4-tert-butoxyphenyl)sulfoxide, bis(4-tert-butoxycarbonyloxyphenyl)sulfoxide, and bis[4-(1-ethoxyethoxy)phenyl]sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis[4-(1-ethoxypropoxy)phenyl]sulfone; diazo compounds such as benzoquinonediazide, naphthoquinonediazide, anthraquinonediazide, diazofluorene, diazotetralone, and diazophenanthrone; quinonediazido group-containing compounds such as complete or partial ester compounds between naphthoquinone-1,2-diazido-5-sulfonic acid chloride and 2,3,4-trihydroxybenzophenone and complete or partial ester compounds between naphthoquinone-1,2-diazido-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate.

The UV absorber may or may not be added to the resist composition depending on the type of resist composition. An appropriate amount of UV absorber, if added, is 0 to 10 parts, more preferably 0.5 to 10 parts, most preferably 1 to 5 parts by weight per 100 parts by weight of the base resin.

For the microfabrication of integrated circuits, any well-known lithography may be used to form a resist pattern from the chemically amplified resist composition of the invention. The composition is applied onto a substrate (e.g., Si, $SiO_2$, SiN, SiON, TiN, WSi, BPSG, SOG, organic anti-reflective coating, etc.) for microfabrication by a suitable coating technique such as spin coating, roll coating, flow coating, dip coating, spray coating or doctor coating. The coating is prebaked on a hot plate at a temperature of 60 to 150° C. for about 1 to 10 minutes, preferably 80 to 140° C. for 1 to 5 minutes.

The resulting resist film is generally 0.1 to 2.0 m thick. Through a photomask having a desired pattern, the resist film is then exposed to radiation, preferably having an exposure wavelength of up to 300 nm, such as UV, deep-UV, electron beam, x-ray, excimer laser light, γ-ray and synchrotron radiation. The preferred light source is a beam from an excimer laser, especially KrF excimer laser, deep UV of 245-255 nm wavelength and ArF excimer laser. The exposure dose is preferably in the range of about 1 to 200 mJ/cm$^2$, more preferably about 10 to 100 mJ/cm$^2$. The film is further baked on a hot plate at 60 to 150° C. for 1 to 5 minutes, preferably 80 to 140° C. for 1 to 3 minutes (post-exposure baking=PEB).

Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray technique. In this way, a desired resist pattern is formed on the substrate. It is appreciated that the resist composition of the invention is best suited for micro-patterning using such actinic radiation as deep UV with a wavelength of 254 to 193 nm, vacuum UV with a wavelength of 157 nm, electron beam, x-ray, excimer laser light, γ-ray and synchrotron radiation. With any of the above-described parameters outside the above-described range, the process may sometimes fail to produce the desired pattern.

In the practice of the invention, the immersion lithography process involving using ArF excimer laser of 193 nm wavelength and feeding a liquid such as water, glycerin or ethylene glycol between the wafer and the projection lens is advantageously applicable.

EXAMPLE

Synthesis Examples, Examples and Comparative Examples are given below for further illustrating the invention, but they are not to be construed as limiting the invention.

Synthesis Example 1

Synthesis of Triphenylsulfonium Chloride

Diphenyl sulfoxide, 40 g (0.2 mole), was dissolved in 400 g of dichloromethane, which was stirred under ice cooling. At a temperature below 20° C., 65 g (0.6 mole) of trimethylsilyl chloride was added dropwise to the solution, which was aged for 30 minutes at the temperature. Then, a Grignard reagent which had been prepared from 14.6 g (0.6 mole) of metallic magnesium, 67.5 g (0.6 mole) of chlorobenzene and 168 g of tetrahydrofuran (THF) was added dropwise at a temperature below 20° C. The reaction solution was aged for one hour, after which 50 g of water at a temperature below 20° C. was added to quench the reaction. To this solution, 150 g of water, 10 g of 12N hydrochloric acid, and 200 g of diethyl ether were further added.

The water layer was separated and washed with 100 g of diethyl ether, yielding an aqueous solution of triphenylsulfonium chloride. The compound in aqueous solution form was used in the subsequent reaction without further isolation.

Synthesis Example 2

Synthesis of 4-tert-butylphenyldiphenylsulfonium bromide

The target compound was obtained by following the procedure of Synthesis Example 1 aside from using 4-tert-butylbromobenzene instead of the chlorobenzene in Synthesis Example 1 and increasing the amount of water for extraction.

Synthesis Example 3

Synthesis of 4-tert-butoxyphenyldiphenylsulfonium chloride

The target compound was obtained by following the procedure of Synthesis Example 1 aside from using 4-tert-butoxychlorobenzene instead of the chlorobenzene in Synthesis Example 1, using dichloromethane containing 5 wt % of triethylamine as the solvent, and increasing the amount of water for extraction.

Synthesis Example 4

Synthesis of tris(4-methylphenyl)sulfonium chloride

The target compound was obtained by following the procedure of Synthesis Example 1 aside from using bis(4-methylphenyl)sulfoxide instead of the diphenyl sulfoxide and 4-chlorotoluene instead of the chlorobenzene in Synthesis Example 1, and increasing the amount of water for extraction.

Synthesis Example 5

Synthesis of tris(4-tert-butylphenyl)sulfonium bromide

The target compound was obtained by following the procedure of Synthesis Example 1 aside from using bis(4-tert-butylphenyl)sulfoxide instead of the diphenyl sulfoxide and 4-tert-butylbromobenzene instead of the chlorobenzene in Synthesis Example 1, and increasing the amount of water for extraction.

Synthesis Example 6

Synthesis of bis(4-tert-butylphenyl)iodonium hydrogen sulfate

A mixture of 84 g (0.5 mole) of tert-butylbenzene, 53 g (0.25 mole) of potassium iodate and 50 g of acetic anhydride was stirred under ice cooling, and a mixture of 35 g of acetic anhydride and 95 g of conc. sulfuric acid was added dropwise at a temperature below 30° C. The resulting solution was aged for 3 hours at room temperature and ice cooled again, after which 250 g of water was added dropwise to quench the reaction. The reaction solution was extracted with 400 g of dichloromethane. The organic layer was discolored by adding 6 g of sodium hydrogen sulfite. The organic layer was washed with 250 g of water three times. The washed organic layer was concentrated in vacuum, obtaining a crude target product. The product was used in the subsequent reaction without further purification.

Synthesis Example 7

Synthesis of Phenacyltetrahydrothiophenium Bromide 88.2 g (0.44 mole) of phenacyl bromide and 39.1 g (0.44 mole) of tetrahydrothiophene were dissolved in 220 g of nitromethane, which was stirred for 4 hours at room temperature. 800 g of water and 400 g of diethyl ether were added to the reaction solution whereupon the mixture separated into two layers. The aqueous layer was taken out, which was an aqueous solution of the target compound, phenacyltetrahydrothiophenium bromide.

Synthesis Example 8

Synthesis of Dimethylphenylsulfonium Hydrogen Sulfate 6.2 g (0.05 mole) of thioanisole and 6.9 g (0.055 mole) of dimethyl sulfate were stirred for 12 hours at room temperature. 100 g of water and 50 ml of diethyl ether were added to the reaction solution whereupon the mixture separated into two layers. The aqueous layer was taken out, which was an aqueous solution of the target compound, dimethylphenylsulfonium hydrogen sulfate.

Synthesis Example 9

Synthesis of triphenylsulfonium 4-benzoyloxy-1,1,2,2-tetrafluorobutanesulfonate In 42 g of dimethyl sulfoxide were dissolved 10.0 g (0.035 mole) of 1,4-dibromo-1,1,2,2-tetrafluorobutane and 5.0 g (0.035 mole) of sodium benzoate, which was stirred at 60° C. for 3.5 hours. The reaction solution was cooled to room temperature, after which toluene and water were added. The organic layer was taken out and washed once with 20 g of an aqueous saturated sodium hydrogen carbonate solution and twice with 20 g of an aqueous saturated sodium chloride solution. The organic layer was concentrated under reduced pressure, obtaining a compound, 4-bromo-3,3,4,4-tetrafluorobutyl benzoate. Colorless oily matter, 4.1 g.

1.7 g (0.020 mole) of sodium hydrogen carbonate and 2.7 g (0.013 mole) of sodium dithionite were dispersed in 11 g of water, after which 3.9 g (0.011 mole) of 4-bromo-3,3,4,4-tetrafluorobutyl benzoate in 10 g of acetonitrile was added. The reaction mixture was stirred at 60° C. for 3 hours. Stirring was stopped, followed by removal of acetonitrile under vacuum and toluene washing. To the water layer taken out, sodium chloride was added whereupon white crystals precipitated. The crystals were extracted with ethyl acetate. This organic layer was washed with a small volume of aqueous saturated sodium chloride solution, followed by removal under vacuum of the solvent and drying. There was obtained 2.7 g of white crystals. The crystals and 0.1 g (0.35 millimole) of sodium tungstate dihydrate were dissolved in 10 g of water, to which 0.8 g (0.0084 mole) of 35% aqueous hydrogen peroxide was added, followed by 2 hours of stirring. The reaction solution was quenched with sodium hydrogen sulfite, and sodium chloride was added thereto whereupon white crystals precipitated. The crystals were extracted with ethyl acetate. This organic layer was washed with a small volume of aqueous saturated sodium chloride solution, followed by vacuum concentration. The concentrate was poured into diisopropyl ether for recrystallization, obtaining 1.9 g of a compound, sodium 4-benzoyloxy-1,1,2,2-tetrafluorobutanesulfonate.

The triphenylsulfonium chloride aqueous solution of Synthesis Example 1 (0.0049 mole) and the sodium 4-benzoyloxy-1,1,2,2-tetrafluorobutanesulfonate (0.0051 mole) synthesized above were stirred in 26 g of dichloromethane. The organic layer was separated and washed three times with 20 g of water. The organic layer was concentrated, obtaining 2.1 g of the target compound, triphenylsulfonium 4-benzoyloxy-1,1,2,2-tetrafluorobutanesulfonate.

Synthesis Example 10

Synthesis of triphenylsulfonium 4-hydroxy-1,1,2,2-tetrafluorobutanesulfonate (PAG1)

In 8 g of methanol was dissolved 2.1 g of triphenylsulfonium 4-benzoyloxy-1,1,2,2-tetrafluorobutanesulfonate synthesized in Synthesis Example 9. The solution was stirred under ice cooling, to which 2.5 g of a 9% sodium hydroxide aqueous solution was added dropwise at a temperature below 10° C. The solution was aged at room temperature for 70 hours, after which 22 g of 1N hydrochloric acid was added under ice cooling for quenching the reaction. The methanol was removed under vacuum. Dichloromethane was added to the organic layer, which was washed three times with water. The organic layer was concentrated and dried, obtaining the target compound. Colorless oily matter, 0.3 g.

Figure 2:
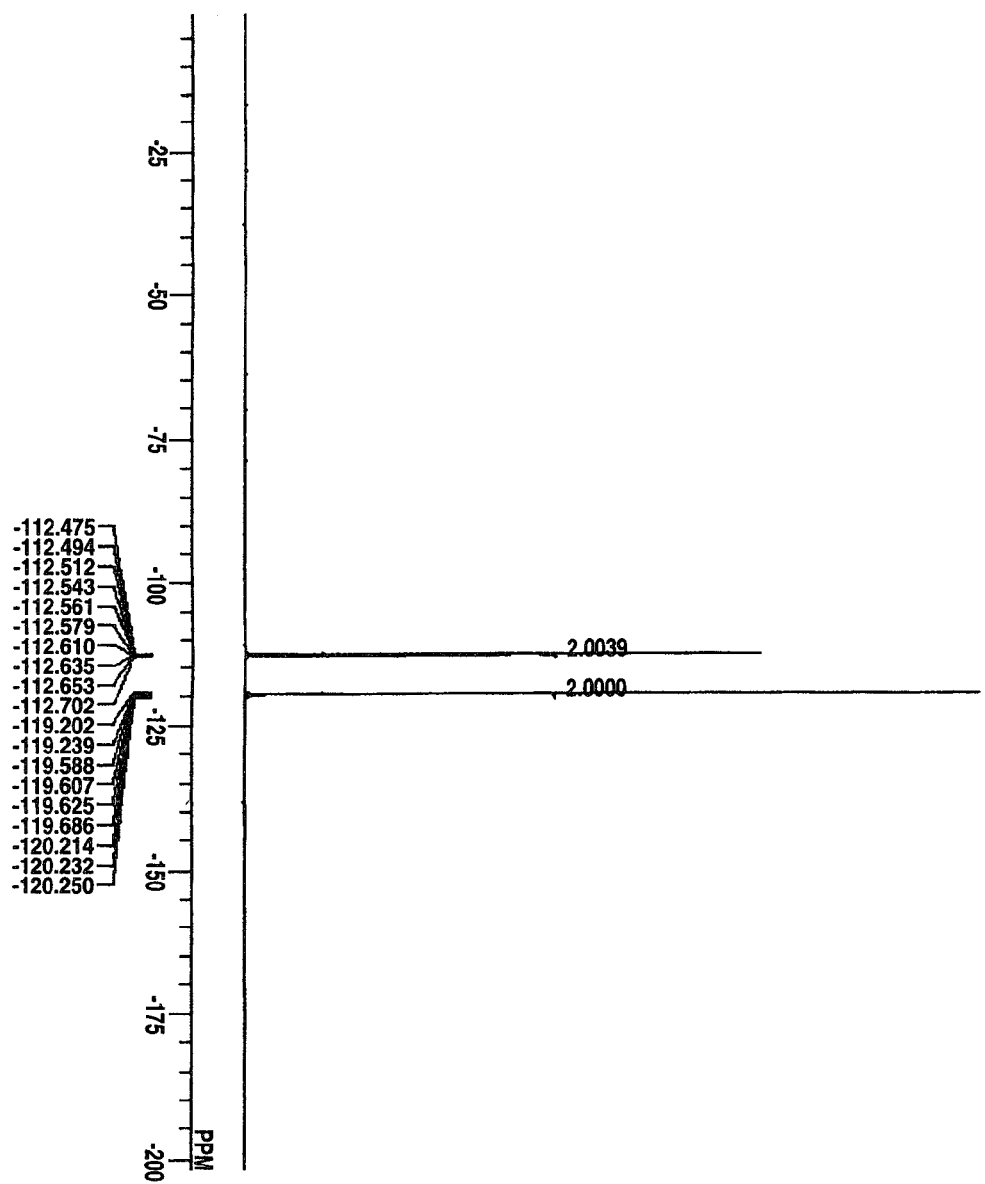
FIG. 2 is a diagram showing the $^{19}$F-NMR/DMSO-$d_6$ spectrum of PAG1 in Synthesis Example 10.

The target compound was analyzed by spectroscopy. The data of IR spectroscopy are shown below. The NMR spectra, $^1$H-NMR (300 MHz in DMSO-$d_6$) and $^{19}$F-NMR (282 MHz in DMSO-$d_6$ (shift standard $CF_3CO_2D$)) are shown in FIGS. 1 and 2.

Infrared absorption spectra (IR, KBr, cm$^{-1}$)
  3442, 3355, 3156, 3089, 3062, 3002, 2950, 2900, 1581, 1477, 1448, 1367, 1265, 1255, 1184, 1164, 1112, 1064, 1052, 1029, 1006, 997, 927, 848, 750, 684, 649, 619

Time-of-flight mass spectrometry (TOFMS, MALDI)
  Positive M$^+$ 263 (corresponding to $(C_6H_5)_3S^+$)
  Negative M$^-$ 225 (corresponding to $HOCH_2CH_2CF_2CF_2SO_3^-$)

Synthesis Examples 11-17

Target compounds were synthesized as in Synthesis Examples 9 and 10 except that the onium salts prepared in Synthesis Examples 2 to 8 were used. The resulting onium salts PAG2 to PAG8 are shown below.

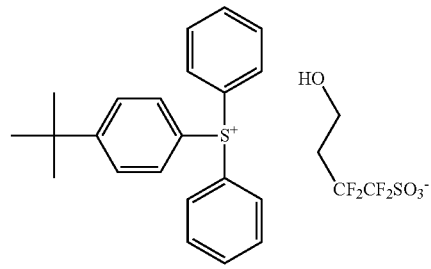
(PAG2)

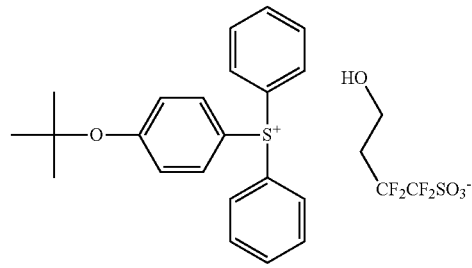
(PAG3)

-continued (PAG4)

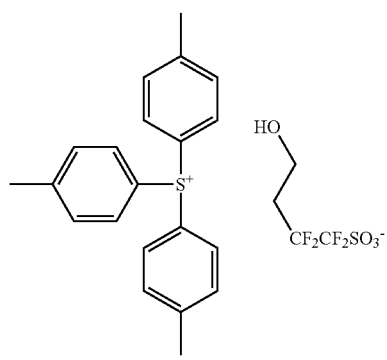

(PAG5)

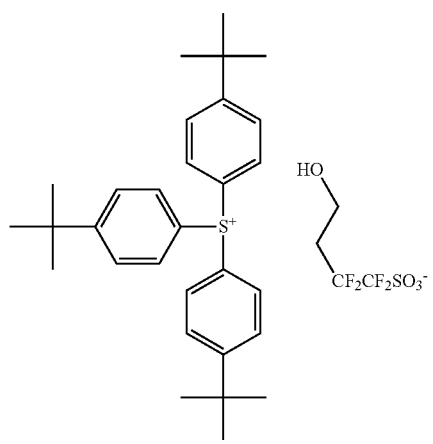

(PAG6)

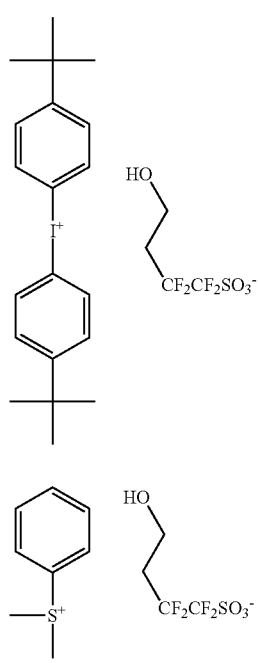

(PAG7)

(PAG8)

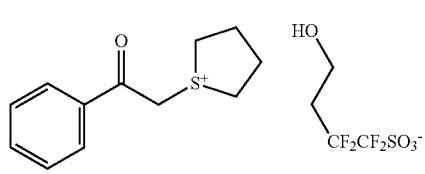

Examples 1-15 & Comparative Examples 1-3

Evaluation of Resist Resolution

Resist compositions were prepared by dissolving the photoacid generators of Synthesis Examples, Polymers 1 to 8 as the base resin, dissolution accelerator DRR1, dissolution inhibitor DRI1, and quencher in a solvent containing 0.01 wt % of surfactant FC-430 (Sumitomo 3M Co., Ltd.) according to the formulation shown in Tables 1 and 2. They were filtered through a Teflon® filter having a pore size of 0.2 μm, giving resist solutions. Polymers 1 to 8, DRR1 and DRI1 are shown below.

(Polymer 1)

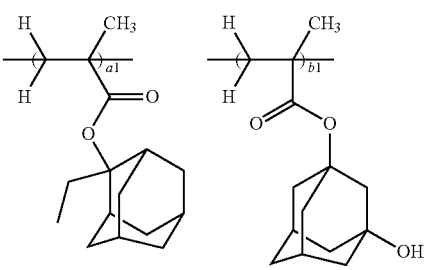

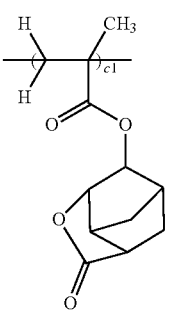

(a1 = 0.35, b1 = 0.20, c1 = 0.45, Mw = 9,200)

(Polymer 2)

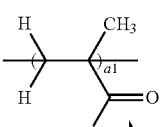

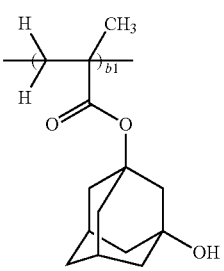

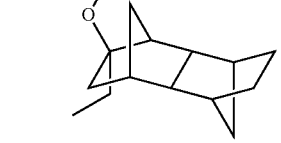

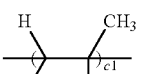

(a1 = 0.30, b1 = 0.25, c1 = 0.45, Mw = 8,300)

(Polymer 3)
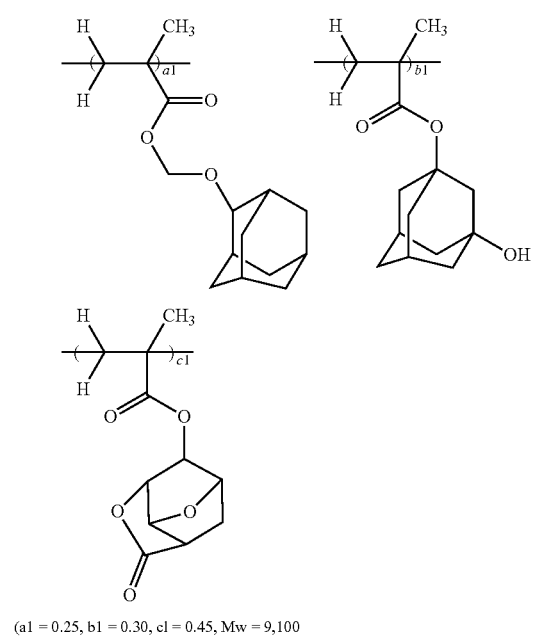
(a1 = 0.25, b1 = 0.30, c1 = 0.45, Mw = 9,100)
(Polymer 4)
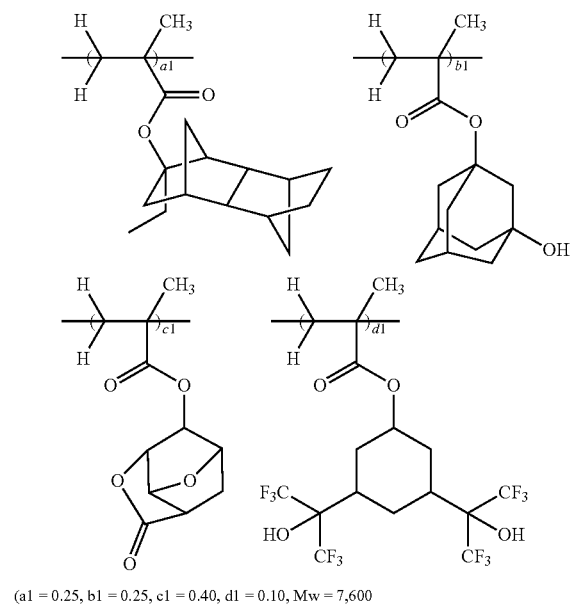
(a1 = 0.25, b1 = 0.25, c1 = 0.40, d1 = 0.10, Mw = 7,600)
(Polymer 5)
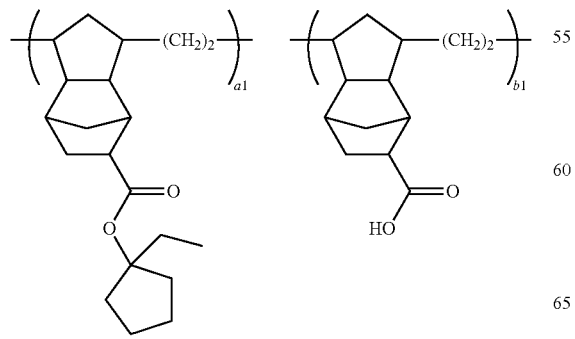
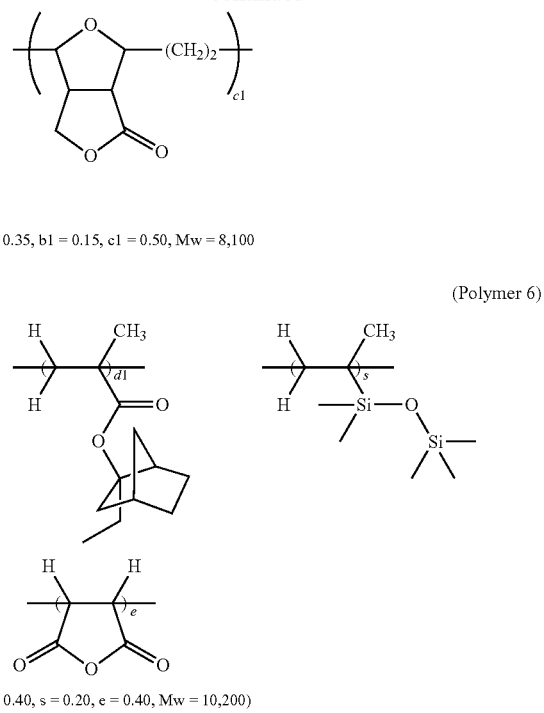
(a1 = 0.35, b1 = 0.15, c1 = 0.50, Mw = 8,100)
(Polymer 6)
(d1 = 0.40, s = 0.20, e = 0.40, Mw = 10,200)
(Polymer 7)
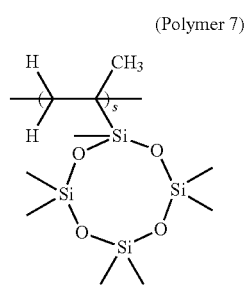
(d1 = 0.45, s = 0.10, e = 0.45, Mw = 12,200)
(Polymer 8)
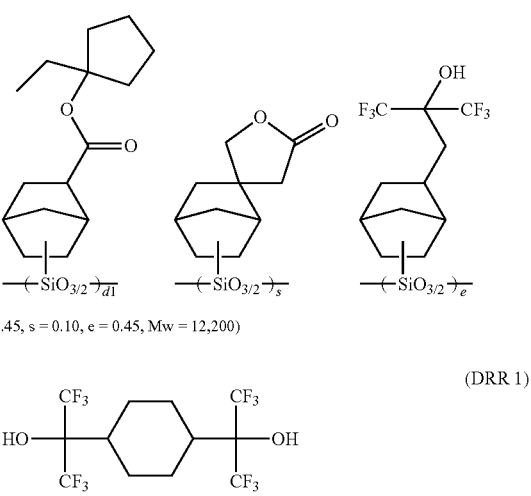
(d1 = 0.45, s = 0.10, e = 0.45, Mw = 12,200)
(DRR 1)
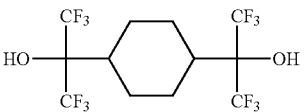

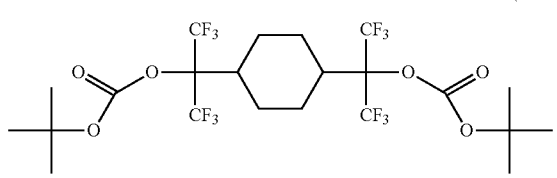

(DRI 1)

An antireflective coating liquid ARC-29A (Nissan Chemical Co., Ltd.) was coated onto a silicon substrate and baked at 200° C. for 60 seconds to form an antireflective coating of 78 nm thick. The resist solution was spin coated onto the antireflective coating and baked on a hot plate at 120° C. for 60 seconds, forming a resist film of 200 nm thick. The resist film was exposed by means of an ArF excimer laser microstepper model S305B (Nikon Corp., NA 0.68, 2/3 annular illumination, Cr mask), post-exposure baked (PEB) at 110° C. for 90 seconds, and developed with a 2.38 wt % aqueous solution of tetramethylammonium hydroxide (TMAH) for 60 seconds.

An optimal exposure dose (sensitivity Eop, mJ/cm$^2$) was the exposure which provided a 1:1 resolution at the top and bottom of a 0.12-m group line-and-space pattern. The minimum line width (m) of a line-and-space pattern which was ascertained separate at this dose was the resolution of a test resist. The formulation and test results of the resist compositions are shown in Tables 1 and 2.

The solvents and quenchers in Tables 1 and 2 are shown below as well as the photoacid generators in Comparative Examples.
Solvent A: propylene glycol monomethyl ether acetate
Solvent B: cyclohexanone
Quencher A: tri-n-octylamine
Quencher B: triethanolamine
Quencher C: trismethoxymethoxyethylamine
Quencher D: tris(2-acetoxyethyl)amine
TPS-NfO: triphenylsulfonium perfluoro-1-butanesulfonate
TPS-PFOS: triphenylsulfonium perfluoro-1-octanesulfonate

TABLE 1

| Formulation (pbw) | Example |||||||||
|---|---|---|---|---|---|---|---|---|---|
| | 1 | 2 | 3 | 4 | 5 | 6 | 7 | 8 | 9 |
| Polymer1 | 80 | | | | | | | | 80 |
| Polymer2 | | 80 | | | | | | | |
| Polymer3 | | | 80 | | | | | | |
| Polymer4 | | | | 80 | | | | | |
| Polymer5 | | | | | 80 | | | | |
| Polymer6 | | | | | | 80 | | | |
| Polymer7 | | | | | | | 80 | | |
| Polymer8 | | | | | | | | 80 | |
| PAG1 | 6 | 6 | 6 | 6 | 6 | 6 | 6 | 6 | |
| PAG2 | | | | | | | | | 6 |
| PAG3 | | | | | | | | | |
| PAG5 | | | | | | | | | |
| PAG6 | | | | | | | | | |
| TPS-NfO | | | | | | | | | |
| TPS-PFOS | | | | | | | | | |
| Quencher A | 0.5 | 0.5 | 0.5 | 0.5 | | | | | |
| Quencher B | | | | | 0.5 | 0.5 | 0.5 | | |
| Quencher C | | | | | | | | 0.5 | 0.5 |
| Quencher D | | | | | | | | | |
| DRR1 | | | | | | | | | |
| DRI1 | | | | | | | | | |
| Solvent A | 800 | 800 | 800 | 800 | | 800 | 800 | 800 | 800 |
| Solvent B | | | | | 800 | | | | |
| Tests |||||||||
| Sensitivity (mJ/cm$^2$) | 22 | 22 | 23 | 24 | 24 | 23 | 22 | 23 | 28 |
| Resolution (m) | 0.11 | 0.11 | 0.11 | 0.11 | 0.12 | 0.11 | 0.11 | 0.11 | 0.11 |

TABLE 2

| Formulation (pbw) | Example |||||| Comparative Example |||
|---|---|---|---|---|---|---|---|---|---|
| | 10 | 11 | 12 | 13 | 14 | 15 | 1 | 2 | 3 |
| Polymer1 | | 40 | | | | | 80 | | |
| Polymer2 | 80 | | 40 | 40 | 80 | 60 | | 80 | 40 |
| Polymer3 | | | | 40 | | | | | 40 |
| Polymer4 | | | 40 | | | | | | |
| Polymer5 | | 40 | | | | 20 | | | |
| Polymer6 | | | | | | | | | |
| Polymer7 | | | | | | | | | |
| Polymer8 | | | | | | | | | |
| PAG1 | | | 6 | | 4 | | | | |
| PAG2 | | | | | | 4 | | | |
| PAG3 | 6 | | | | | | | | |
| PAG5 | | | | | 6 | | | | |
| PAG6 | | 6 | | | | | | | |
| TPS-NfO | | | | | | | 1 | 4 | 2 |

TABLE 2-continued

| Formulation (pbw) | Example | | | | | | Comparative Example | | |
|---|---|---|---|---|---|---|---|---|---|
| | 10 | 11 | 12 | 13 | 14 | 15 | 1 | 2 | 3 |
| TPS-PFOS | | | | | 1 | | | 4 | 3 |
| Quencher A | | | | | | 0.5 | 0.5 | 0.5 | 0.5 |
| Quencher B | | | | | | | | | |
| Quencher C | 0.5 | | | 0.5 | 0.5 | | | | |
| Quencher D | | 0.5 | 0.5 | | | | | | |
| DRR1 | | | | | | 10 | | | |
| DRI1 | | | | | 10 | | | | |
| Solvent A | 800 | 600 | 800 | 800 | 800 | 600 | 800 | 800 | 800 |
| Solvent B | | 200 | | | | 200 | | | |
| Tests | | | | | | | | | |
| Sensitivity (mJ/cm$^2$) | 30 | 24 | 33 | 35 | 24 | 28 | 26 | 30 | 28 |
| Resolution (m) | 0.11 | 0.11 | 0.12 | 0.11 | 0.11 | 0.11 | 0.11 | 0.11 | 0.11 |

Next, simulative immersion photolithography was carried out using the resist compositions of Examples 1, 3, 9 and Comparative Example 1. Specifically, a resist film of 125 nm thick was formed on a wafer by a procedure as described above and exposed by means of an ArF excimer laser microstepper model S307E (Nikon Corp., dipole). Immediately after the exposure, deionized water was fed over the entire surface of the wafer, whereby the exposed surface of resist was immersed in deionized water for 60 seconds (puddle). The wafer was rotated to spin off the water, followed by ordinary PEB and development. The number of defects in the pattern formed after development was counted by a wafer inspection system WINWIN 50-1200L (Tokyo Seimitsu Co., Ltd.). A defect density was computed therefrom.

Defect density(/cm$^2$)=(total number of detected defects)/(test area).

Pattern formed: repetitive pattern of 80 nm pitch, 160 nm line-and-space

Defect detection: light source UV, detection pixel size 0.125 μm, cell-to-cell mode Additionally, the pattern profile in resist cross-section was observed under a scanning electron microscope. The results are shown in Table 3.

TABLE 3

| | Defect density (/cm$^2$) | Pattern profile |
|---|---|---|
| Example 1 | ≦0.05 | rectangular |
| Example 3 | ≦0.05 | rectangular |
| Example 9 | ≦0.05 | rectangular |
| Comparative Example 1 | 10 | extreme T-top |

As is evident from Tables 1 to 3, the resist compositions of the invention have a high sensitivity and high resolution and invite neither profile changes nor defects during a long term of water rinsing as compared with the prior art composition, suggesting an ability to comply with the immersion photolithography.

Japanese Patent Application No. 2006-176044 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonate salt having the general formula (1):

$$HOCH_2CH_2CF_2CF_2SO_3^- M^+ \quad (1)$$

wherein M$^+$ is a lithium, sodium, potassium, ammonium, or tetramethylammonium ion.

* * * * *